United States Patent
Yamada

(10) Patent No.: US 9,486,124 B2
(45) Date of Patent: Nov. 8, 2016

(54) ADVANCE AND RETREAT ASSIST TOOL FOR ENDOSCOPIC TREATMENT INSTRUMENT

(71) Applicant: OLYMPUS CORPORATION, Tokyo (JP)

(72) Inventor: Tetsuhiro Yamada, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/477,201

(22) Filed: Sep. 4, 2014

(65) Prior Publication Data

US 2015/0045617 A1 Feb. 12, 2015

Related U.S. Application Data

(63) Continuation of application No. PCT/JP2014/050008, filed on Jan. 6, 2014.

(30) Foreign Application Priority Data

Feb. 27, 2013 (JP) ................. 2013-037221

(51) Int. Cl.
| | |
|---|---|
| *A61B 1/00* | (2006.01) |
| *A61B 1/04* | (2006.01) |
| *A61B 1/018* | (2006.01) |
| *G02B 23/24* | (2006.01) |
| *A61B 17/00* | (2006.01) |

(52) U.S. Cl.
CPC ........... *A61B 1/00133* (2013.01); *A61B 1/018* (2013.01); *A61B 17/00234* (2013.01); *G02B 23/2476* (2013.01); *A61B 2017/0034* (2013.01)

(58) Field of Classification Search
USPC ........ 600/104, 106, 107, 121–125, 139–154, 600/102, 117, 114, 115, 131, 459, 462–464, 600/466, 471, 585; 606/1, 205–209, 167, 606/170, 172, 185
See application file for complete search history.

(56) References Cited

U.S. PATENT DOCUMENTS

2014/0171735 A1\* 6/2014 Galperin ............ A61B 1/00066
600/106

FOREIGN PATENT DOCUMENTS

| | | |
|---|---|---|
| JP | B1-49-26676 | 7/1974 |
| JP | A-9-276211 | 10/1997 |
| JP | A-2001-170006 | 6/2001 |
| JP | A-2003-265406 | 9/2003 |
| JP | A-2005-73798 | 3/2005 |
| JP | A-2005-218755 | 8/2005 |
| JP | A-2010-57919 | 3/2010 |
| JP | A-2010-149011 | 7/2010 |

OTHER PUBLICATIONS

International Search Report issued in International Application No. PCT/JP2014/050008 mailed Jan. 28, 2014.

\* cited by examiner

*Primary Examiner* — Ryan Henderson
(74) *Attorney, Agent, or Firm* — Oliff PLC

(57) ABSTRACT

An advance and retreat assist tool includes a base unit, a first tubular member, a rotary portion and an advance and retreat mechanism. The advance and retreat assist tool further includes a hinge mechanism which switches to either a coaxial condition or a slanted condition.

13 Claims, 19 Drawing Sheets

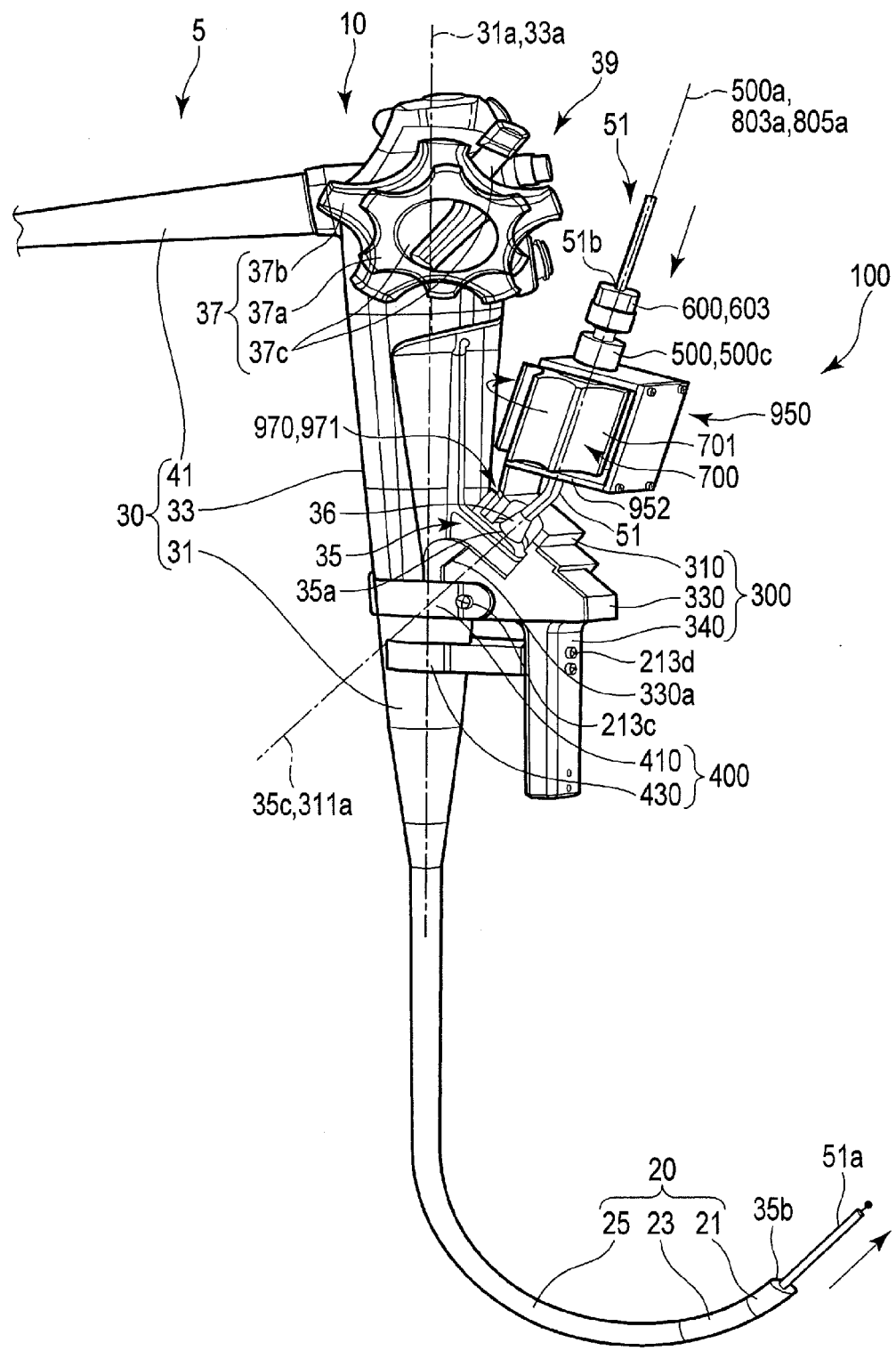
F I G. 1A

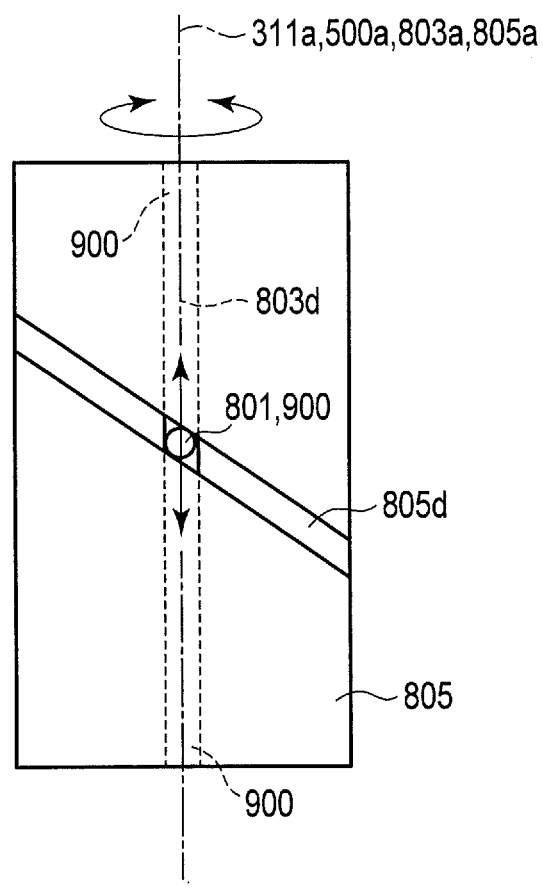
F I G. 3C

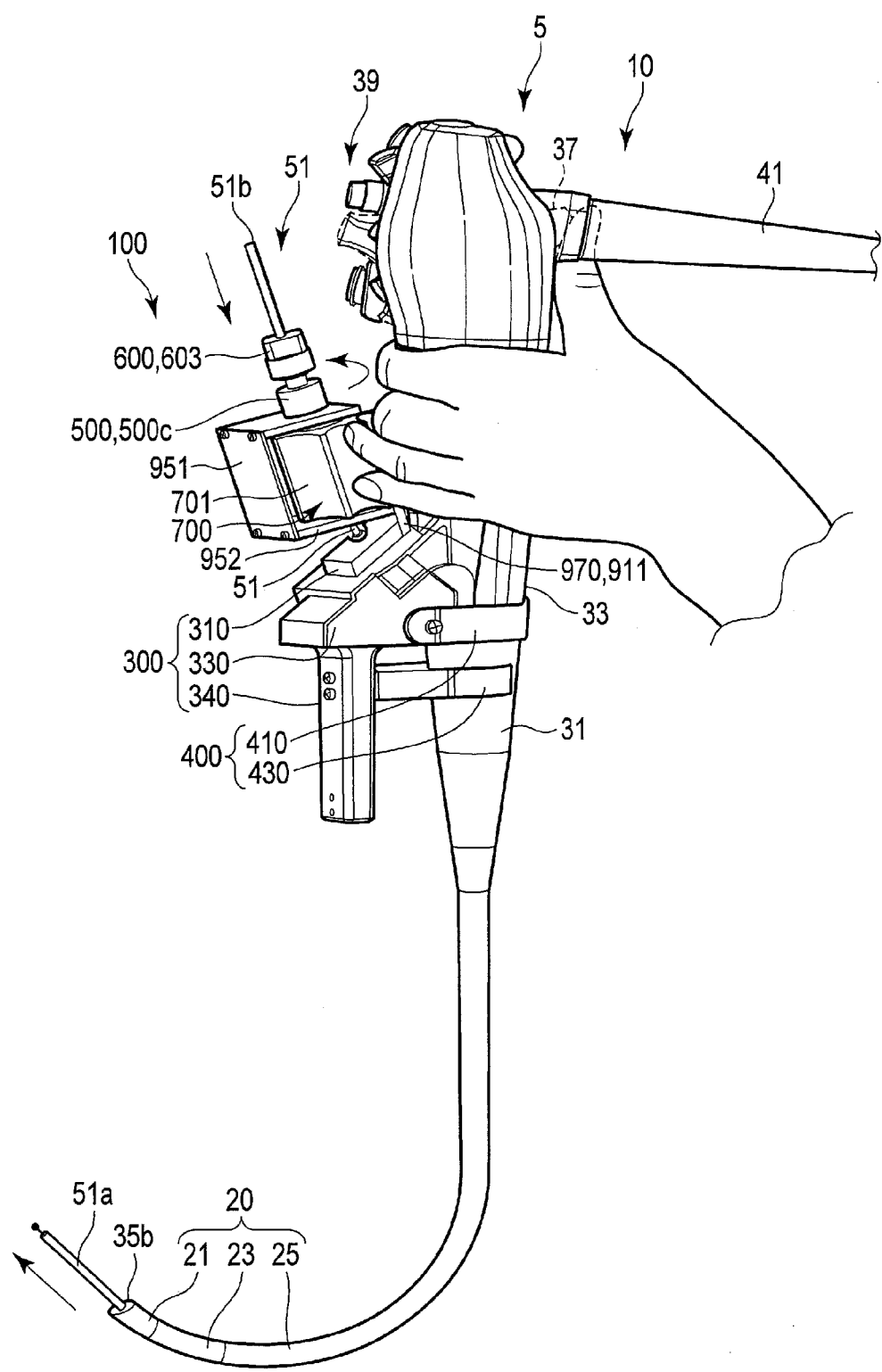
F I G. 5A

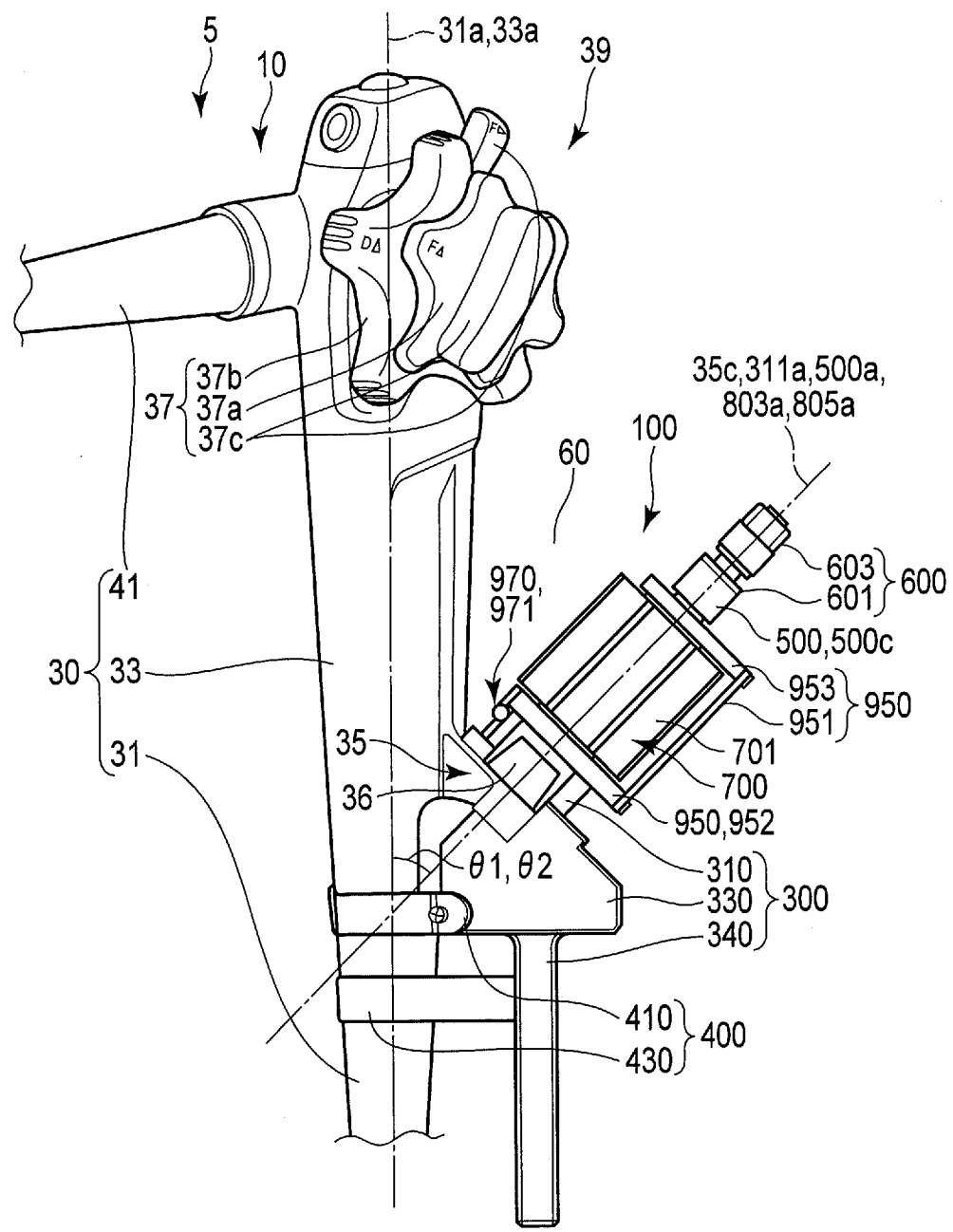
F I G. 5B

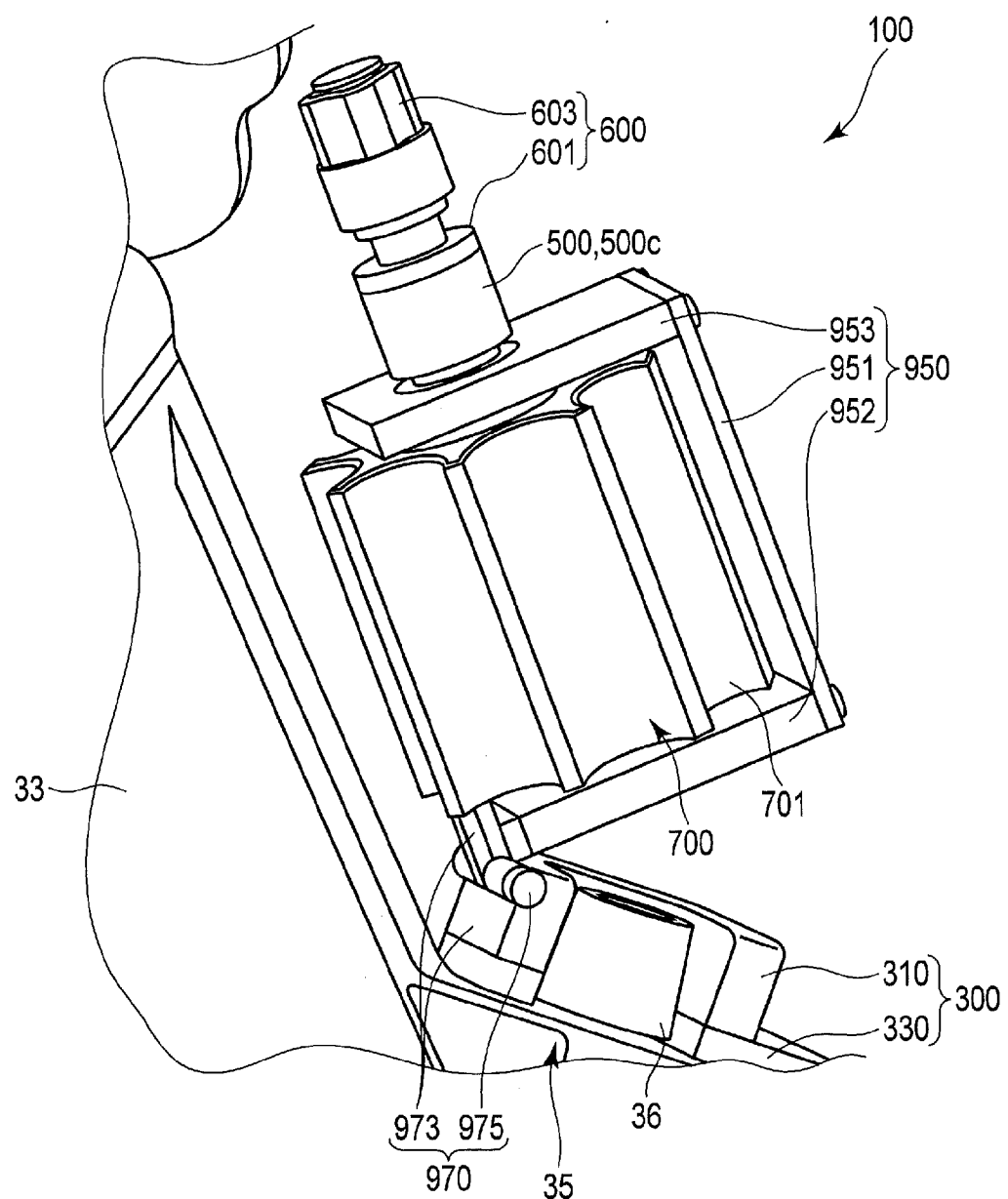
F I G. 6

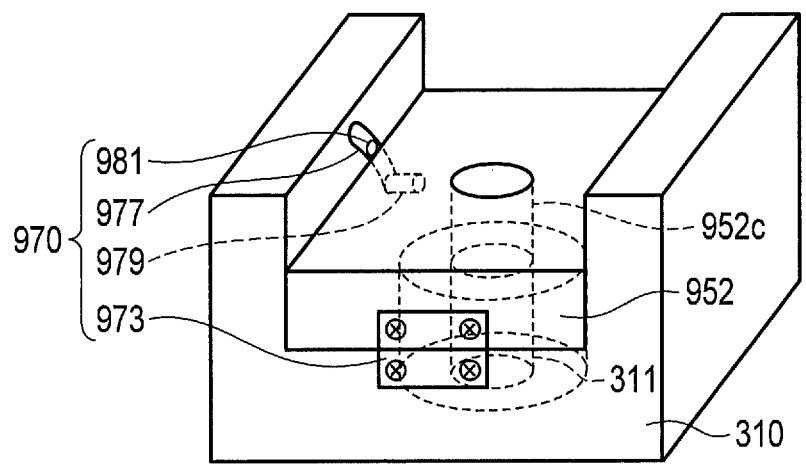
F I G. 7A
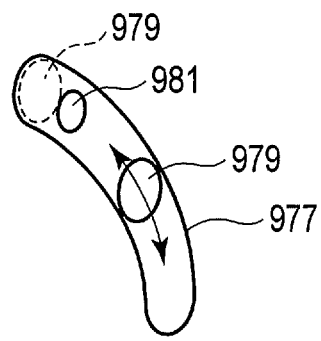
F I G. 7B

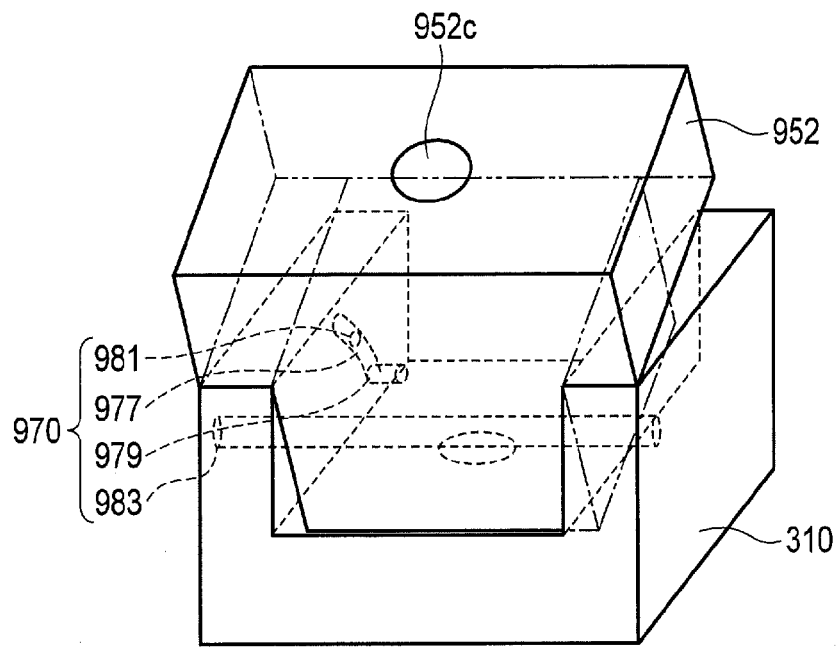
F I G. 8A
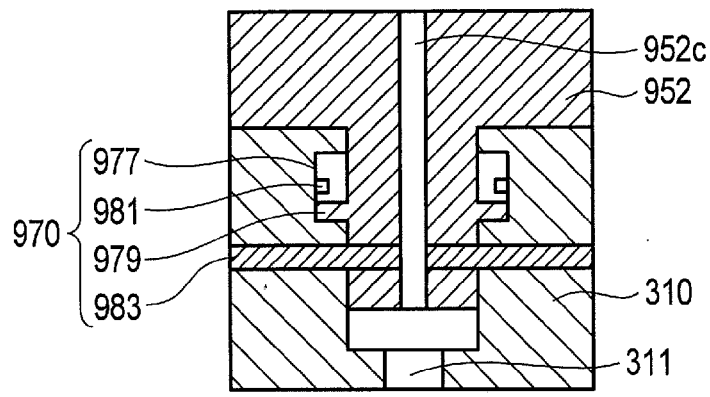
F I G. 8B

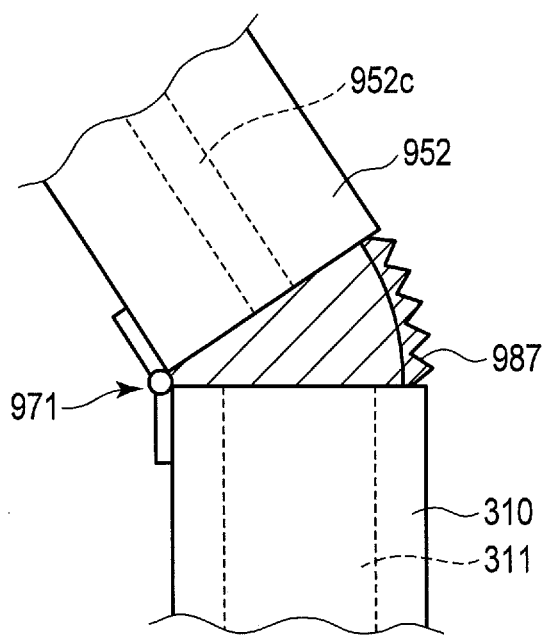
F I G. 10

ADVANCE AND RETREAT ASSIST TOOL FOR ENDOSCOPIC TREATMENT INSTRUMENT

CROSS-REFERENCE TO RELATED APPLICATIONS

This application is a Continuation application of PCT Application No. PCT/JP2014/050008, filed Jan. 6, 2014 and based upon and claiming the benefit of priority from prior Japanese Patent Application No. 2013-037221, filed Feb. 27, 2013, the entire contents of all of which are incorporated herein by reference.

BACKGROUND OF THE INVENTION

1. Field of the Invention

The present invention relates to an advance and retreat assist tool for an endoscopic treatment instrument.

2. Description of the Related Art

For example, Jpn. Pat. Appln. KOKAI Publication No. 2010-057919, Jpn. Pat. Appln. KOKAI Publication No. 2010-194011, Jpn. Pat. Appln. KOKAI Publication No. 2005-073798, and Jpn. Pat. Appln. KOKAI Publication No. 9-276211 have each disclosed an advance and retreat assist tool for an endoscopic treatment instrument which assists a treatment instrument of an endoscope in advancing and retreating.

For example, in Jpn. Pat. Appln. KOKAI Publication No. 2010-057919, Jpn. Pat. Appln. KOKAI Publication No. 2010-194011, Jpn. Pat. Appln. KOKAI Publication No. 2005-073798, and Jpn. Pat. Appln. KOKAI Publication No. 9-276211, the advance and retreat assist tool is attached to a treatment instrument insertion hole portion so that the advance and retreat assist tool is provided straight along the central axis direction of the treatment instrument insertion hole portion provided in a treatment instrument insertion portion. The central axis direction of the treatment instrument insertion hole portion is slanted relative to the central axis direction of a grasping portion. Thus, the advance and retreat assist tool is slanted relative to the central axis direction of the grasping portion.

BRIEF SUMMARY OF THE INVENTION

An aspect of advance and retreat assist tool for an endoscopic treatment instrument of the present is the advance and retreat assist tool includes: a base unit which comprises a part where the endoscopic treatment instrument to be inserted into an endoscope passes and which is fixed to the endoscope to face a treatment instrument insertion hole portion of the endoscope; a first tubular member provided so that the first tubular member is able to be provided coaxially with the first central axis of the treatment instrument insertion hole portion, the endoscopic treatment instrument being inserted into and fixed to the first tubular member; a rotary portion into which the first tubular member is inserted and which rotates around the same axis as the first tubular member; an advance and retreat mechanism which converts a rotation force during the rotation of the rotary portion to an advance and retreat force along the axial direction of the first tubular member to advance and retreat the first tubular member; a support unit which supports the first tubular member so that the first tubular member is advanced and retreated by the advance and retreat mechanism; and a hinge mechanism provided to connect the base unit and the support unit, the hinge mechanism switching to either a coaxial condition where the axis of the rotary portion is provided coaxially with the central axis of the treatment instrument insertion hole portion when the endoscopic treatment instrument is inserted into or removed from the endoscope or a slanted condition where the axis of the rotary portion is slanted relative to the central axis of the treatment instrument insertion hole portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a schematic diagram showing how an advance and retreat assist tool according to a first embodiment of the present invention is attached to an endoscope and how a treatment instrument advances;

FIG. 3C is a front view showing the relation between a protrusion portion, a long opening portion, and a spiral opening portion during the advance and retreat of the treatment instrument;

FIG. 5A is a schematic diagram showing how a bending operation portion and a rotation portion are operated by the fingers of the left hand of a surgeon while a grasping portion is being grasped by the left hand in the endoscope to which the advance and retreat assist tool is attached;

FIG. 5B is a schematic diagram in which the angle θ1=the angle θ2, the condition is the coaxial condition, a clearance between the grasping portion and the rotation portion is widest, and the interruption of grasping by the advance and retreat assist tool is eliminated;

FIG. 6 is an exploded perspective view of the part mainly around a hinge mechanism according to a first modification of the first embodiment;

FIG. 7A is a perspective view of the hinge mechanism according to a second modification of the first embodiment;

FIG. 7B is a diagram showing the relation between a guide groove portion, a protrusion portion, and a lock portion in the hinge mechanism shown in FIG. 7A;

FIG. 8A is a perspective view of the hinge mechanism according to a third modification of the first embodiment;

FIG. 8B is a front sectional view of FIG. 8A;

FIG. 10 is a diagram showing a corrugated protective member according to a fifth modification of the first embodiment.

DETAILED DESCRIPTION OF THE INVENTION

Hereinafter, embodiments of the present invention will be described in detail with reference to the drawings.

First Embodiment

Configuration

The first embodiment is described with reference to FIG. 1A, FIG. 1B, FIG. 1C, FIG. 2A, FIG. 2B, FIG. 3A, FIG. 3B, FIG. 3C, FIG. 4A, FIG. 4B, FIG. 4C, FIG. 5A, FIG. 5B, and FIG. 5C. In some of the drawings, some components are not shown for clarity.

Figure 3A:
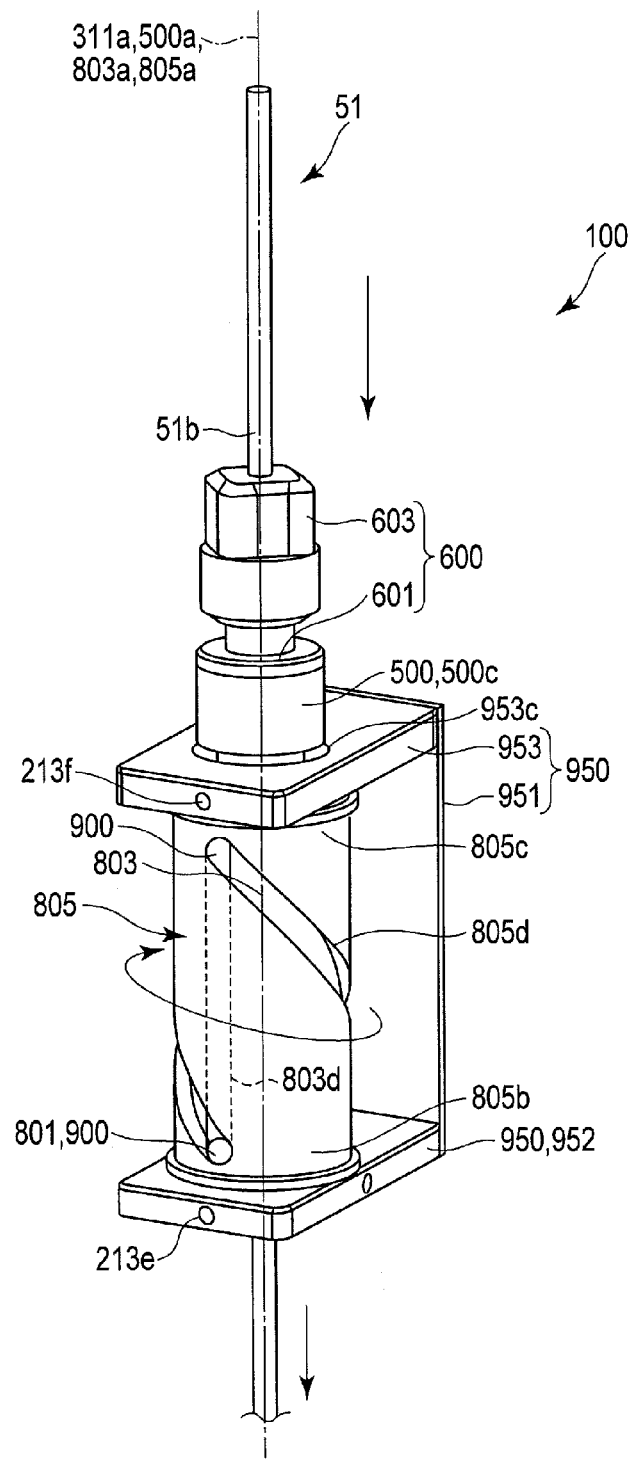
FIG. 3A is a perspective view of the advance and retreat assist tool during the advance of the treatment instrument.
Figure 4A:
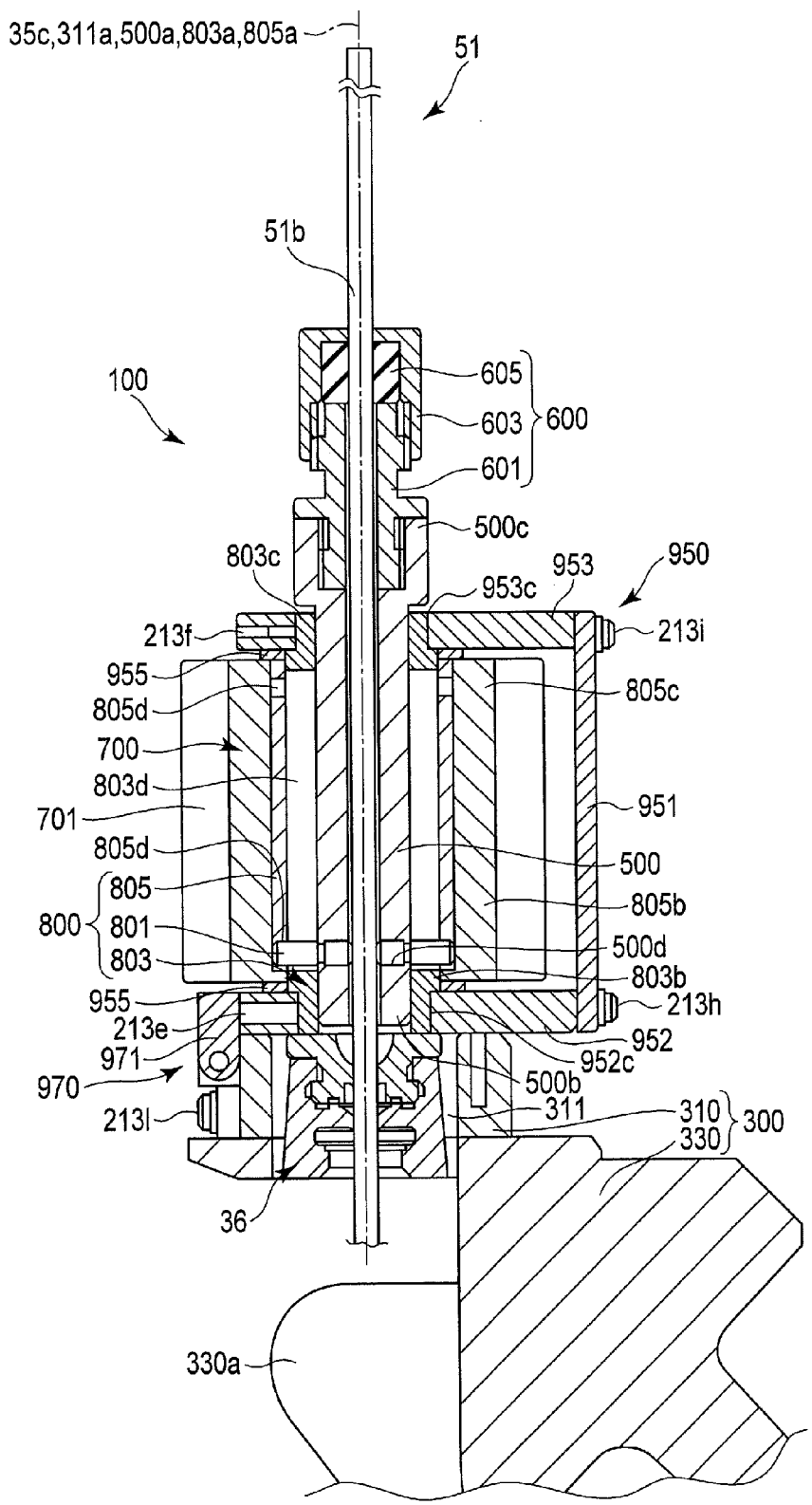
FIG. 4A is a sectional view of the advance and retreat assist tool in the coaxial condition.

As shown in FIG. 1A, FIG. 3A, and FIG. 4A, the advance of a first tubular member 500 means that the first tubular member 500 moves along the direction of a second central axis 500a so that the first tubular member 500 is inserted into a second tubular member 803.

Figure 1B:
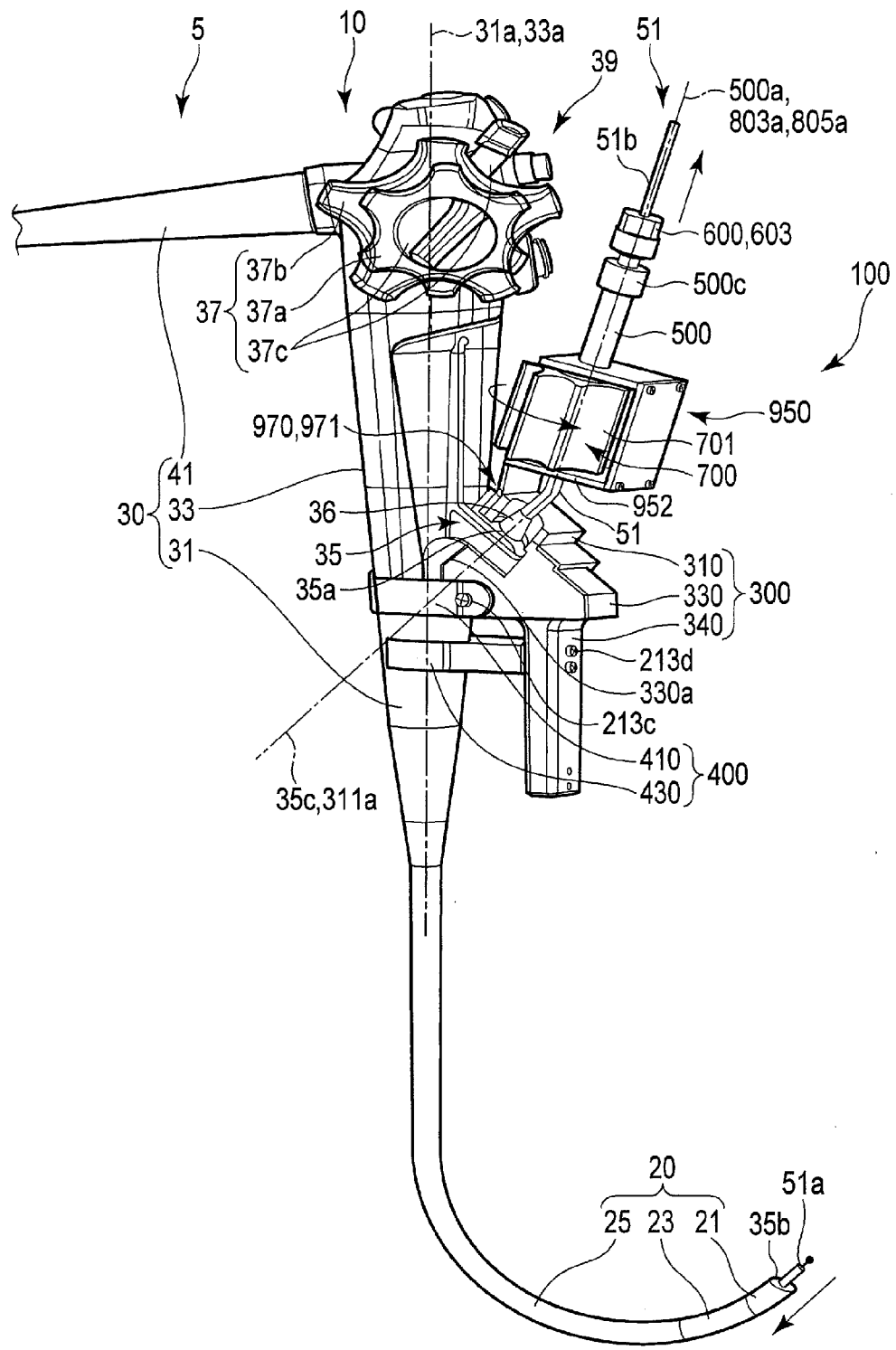
FIG. 1B is a schematic diagram showing how the advance and retreat assist tool is attached to the endoscope and how the treatment instrument retreats.
Figure 3B:
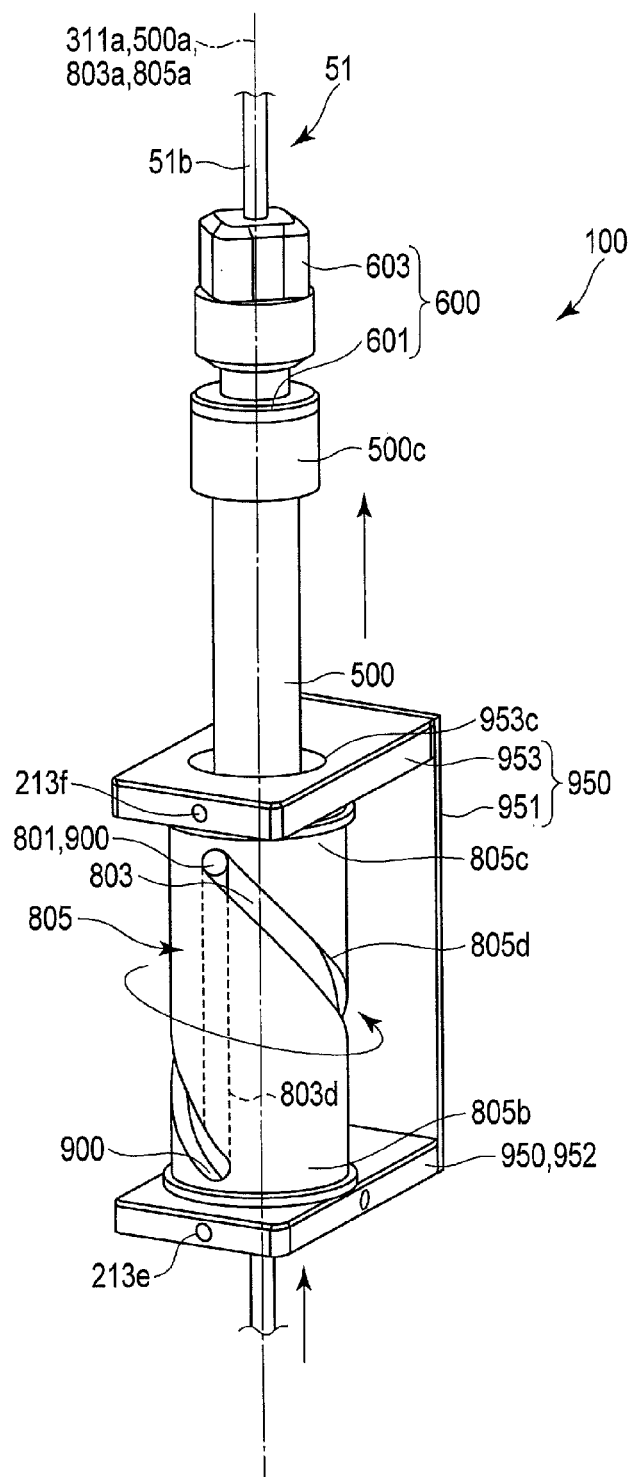
FIG. 3B is a perspective view of the advance and retreat assist tool during the retreat of the treatment instrument.
Figure 4B:
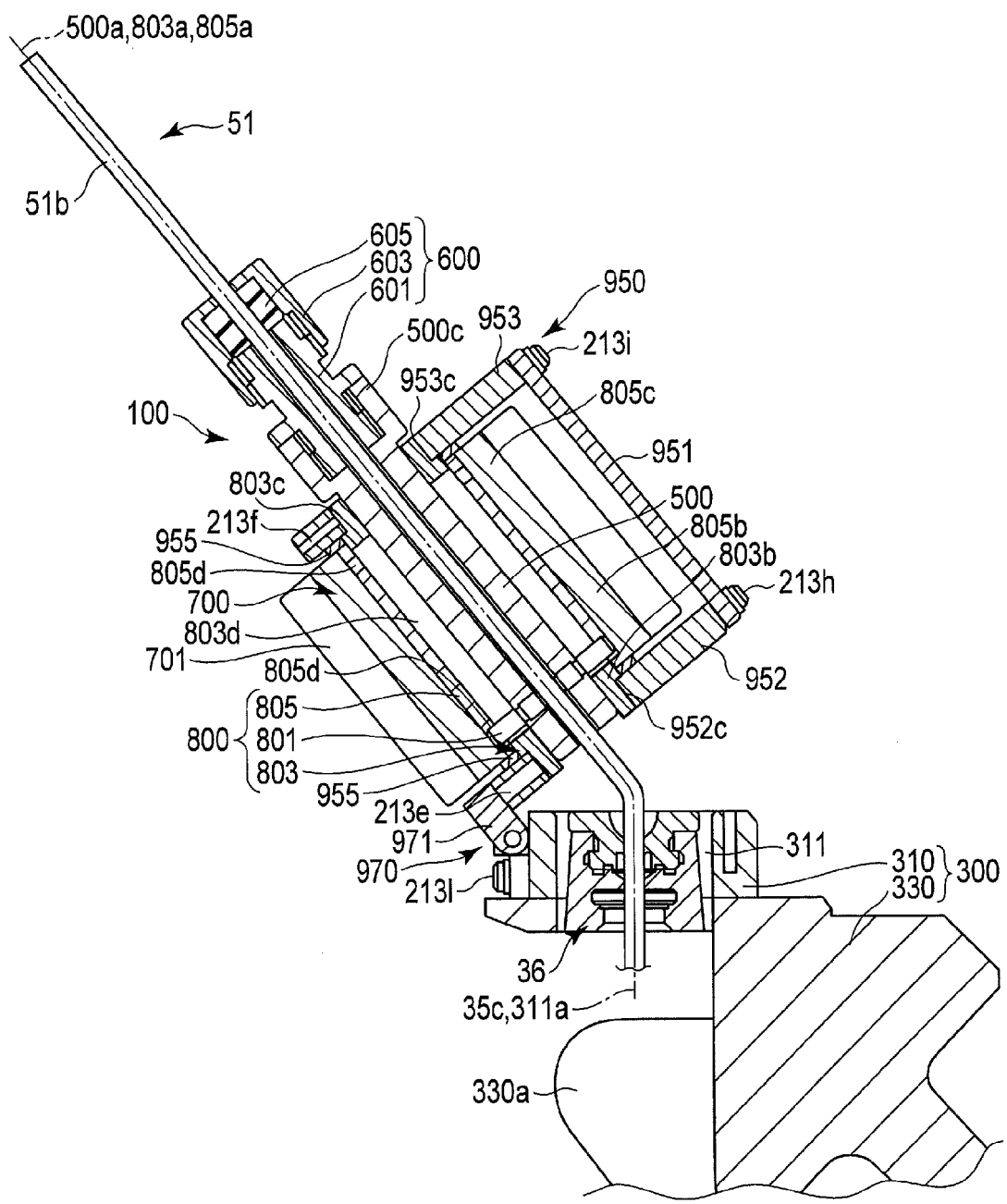
FIG. 4B is a sectional view of the advance and retreat assist tool during the advance of the treatment instrument in the slanted condition.

As shown in FIG. 1B, FIG. 3B, and FIG. 4B, the retreat of the first tubular member 500 means that the first tubular member 500 moves along the direction of the second central axis 500a so that the first tubular member 500 is removed from the second tubular member 803.

As shown in FIG. 1A, FIG. 1B, FIG. 3A, FIG. 3B, FIG. 4A, and FIG. 4B, for example, the advance and retreat of the first tubular member 500 include the advance of the first tubular member 500 and the retreat of the first tubular member 500.

As shown in FIG. 1A, FIG. 3A, and FIG. 4A, for example, the advance of a treatment instrument 51 means that the treatment instrument 51 moves so that the treatment instrument 51 moves to the side of a distal hard portion 21 from the side of an operation portion 30 and a distal end portion 51a of the treatment instrument 51 projects outward from the inside of an insertion portion 20 via a distal opening portion 35b in response to the advance of the first tubular member 500.

As shown in FIG. 1B, FIG. 3B, and FIG. 4B, for example, the retreat of the treatment instrument 51 means that the treatment instrument 51 moves so that the treatment instrument 51 moves to the side of the operation portion 30 from the side of the distal hard portion 21 and the distal end portion 51a of the treatment instrument 51 is housed in the insertion portion 20 from the outside via the distal opening portion 35b in response to the retreat of the first tubular member 500.

As shown in FIG. 1A, FIG. 1B, FIG. 3A, FIG. 3B, FIG. 4A, and FIG. 4B, for example, the advance and retreat of the treatment instrument 51 include the advance of the treatment instrument 51 and the retreat of the treatment instrument 51.

[Endoscopic System 5]

As shown in FIG. 1A and FIG. 1B, an endoscopic system 5 has an endoscope 10, the endoscopic treatment instrument (hereinafter, treatment instrument 51), and an advance and retreat assist tool 100 for the treatment instrument 51.

[Endoscope 10]

The endoscope 10 has a hollow and elongated insertion portion 20 to be inserted into, for example, a body cavity, and the operation portion. 30 which is coupled to the proximal end portion of the insertion portion 20 and which operates the endoscope 10.

[Insertion Portion 20]

The insertion portion 20 has the distal hard portion 21, a bending portion 23, and a flexible tubular portion 25 from the distal end portion side of the insertion portion 20 to the proximal end portion side of the insertion portion 20. The proximal end portion of the distal hard portion 21 is coupled to the distal end portion of the bending portion 23, and the proximal end portion of the bending portion 23 is coupled to the distal end portion of the flexible tubular portion 25.

The distal hard portion 21 is the distal end portion of the insertion portion 20, and is hard and unbendable. The distal hard portion 21 has the distal opening portion 35b, and an unshown observation window included in an unshown observation optical system. The distal hard portion 21 also has an unshown pair of illumination windows which are provided across the observation window and which are included in an unshown illumination optical system, and a nozzle which supplies air and water to the observation window. The distal opening portion 35b, the observation window, the illumination windows, and the nozzle are provided in a distal end face of the distal hard portion 21.

The bending portion 23 is bent in a desired direction, for example, in an upward, downward, leftward, or rightward direction by the operation of a later-described bending operation portion 37. When the bending portion 23 is bent, the position and direction of the distal hard portion 21 are changed. An observation target is illuminated by unshown illumination light, and the observation target is enters into an observation field. This observation target is, for example, an affected part or a lesion in a subject (e.g., body cavity).

The flexible tubular portion 25 has desired flexibility. Therefore, the flexible tubular portion 25 is bent by an external force. The flexible tubular portion 25 is a tubular member extending from a later-described body portion 31 in the operation portion 30.

[Operation Portion 30]

The operation portion 30 has the body portion 31 from which the flexible tubular portion 25 extends, a grasping portion 33 which is coupled to the proximal end portion of the body portion 31 and which is grasped by a surgeon who operates the endoscope 10, and a universal cord 41 connected to the grasping portion 33.

[Grasping Portion 33]

The grasping portion 33 has a treatment instrument insertion portion 35, the bending operation portion 37 which is operated to bend the bending portion 23, and a switch portion 39. The treatment instrument insertion portion 35 is provided on the distal end portion side of the grasping portion 33. The bending operation portion 37 and the switch portion 39 are provided on the proximal end portion side of the grasping portion 33. As shown in FIG. 5A, the grasping portion 33 is grasped by the left hand of the surgeon, and the bending operation portion 37 and the switch portion 39 are operated by the fingers of the left hand.

[Treatment Instrument Insertion Portion 35]

The treatment instrument insertion portion 35 branches off from the grasping portion 33. Thus, as shown in FIG. 1A and FIG. 1B, the central axis direction of the treatment instrument insertion portion 35 is slanted relative to the direction of a central axis 33a of the grasping portion 33.

As shown in FIG. 1A and FIG. 1B, the treatment instrument insertion portion 35 has a treatment instrument insertion hole portion 35a which is provided at the end portion of the treatment instrument insertion portion 35 and which is used to insert the treatment instrument 51 into the endoscope 10.

The treatment instrument insertion hole portion 35a is coupled to the proximal end portion of an unshown treatment instrument insertion channel. The treatment instrument insertion channel is provided inside the insertion portion 20, and provided from the flexible tubular portion 25 to the distal hard portion 21 via the bending portion 23. The distal end portion of the treatment instrument insertion channel is in communication with the distal opening portion 35b provided in the distal hard portion 21. The treatment instrument insertion hole portion 35a is an insertion hole portion used to insert the treatment instrument 51 into the treatment instrument insertion channel.

As shown in FIG. 1A and FIG. 1B, a central axis 35c of the treatment instrument insertion hole portion 35a is provided coaxially with the central axis of the treatment instrument insertion portion 35, and is thus slanted relative to the central axis 33a of the grasping portion 33. The direction of the central axis 35c is slanted relative to the direction of the central axis 33a of the grasping portion 33.

As shown in FIG. 1A, FIG. 1B, FIG. 4A, FIG. 4B, FIG. 5A, FIG. 5B, and FIG. 5C, the treatment instrument insertion portion 35 further has a cylindrical treatment instrument insertion cap 36 to be inserted into the treatment instrument insertion hole portion 35a. The treatment instrument insertion cap 36 is made of, for example, a metal. The central axis of the treatment instrument insertion cap 36 is provided coaxially with the central axis 35c of the treatment instrument insertion hole portion 35a. Thus, the treatment instrument insertion cap 36 is slanted relative to the grasping portion 33. When the cylindrical treatment instrument insertion cap 36 is disposed in the treatment instrument insertion hole portion 35a, the treatment instrument insertion cap 36 is in communication with the treatment instrument insertion channel.

The treatment instrument 51 is inserted into the treatment instrument insertion channel from the treatment instrument insertion cap 36 via the treatment instrument insertion hole portion 35a, and pressed to the side of the distal hard portion 21. As shown in FIG. 1A and FIG. 1B, the treatment instrument 51 is then projected from the distal opening portion 35b.

As shown in FIG. 1A, FIG. 1B, FIG. 4A, FIG. 4B, FIG. 5A, FIG. 5B, and FIG. 5C, the advance and retreat assist tool 100 is attached to the treatment instrument insertion portion 35 including the treatment instrument insertion cap 36. In this case, the treatment instrument insertion cap 36 is provided in a first hole portion 311 of a later-described base member 310. The treatment instrument insertion cap 36 has a distal end portion to be inserted into the treatment instrument insertion hole portion 35a, and a proximal end portion which projects outward from the treatment instrument insertion hole portion 35a and which is exposed to the outside.

[Bending Operation Portion 37]

The bending operation portion 37 has a horizontal bending operation knob 37a which is operated to horizontally bend the bending portion 23, a vertical bending operation knob 37b which is operated to vertically bend the bending portion 23, and a fixing knob 37c which fixes the position of the bent bending portion 23.

[Switch Portion 39]

The switch portion 39 is operated by the hand of the surgeon when the grasping portion 33 is grasped by the surgeon. The switch portion 39 is operated during the operation of various functions of the endoscope such as air supply, water supply, suction, and photography.

[Universal Cord 41]

The universal cord 41 has an unshown connector which can be attached to and removed from an unshown control apparatus.

[Treatment Instrument 51]

The treatment instrument 51 is formed by, for example, an elongated linear member.

[Advance and Retreat Assist Tool 100]

As shown in FIG. 1A and FIG. 1B, the advance and retreat assist tool 100 is removably attached to the endoscope 10, in particular, the treatment instrument insertion portion 35. The advance and retreat assist tool 100 assists the treatment instrument 51 in advancing and retreating along the longitudinal axis direction of the treatment instrument 51. The treatment instrument 51 is inserted in the endoscope 10 from the treatment instrument insertion cap 36 via the treatment instrument insertion hole portion 35a. The distal end portion 51a of the treatment instrument 51 can project from the distal opening portion 35b.

As shown in FIG. 1A FIG. 1B, FIG. 5A, FIG. 5B, and FIG. 5C, the advance and retreat assist tool 100 has a base unit 300, and a fixing unit 400 which fixes the base unit 300 to the endoscope 10. As shown in FIG. 1A FIG. 1B, FIG. 5A, FIG. 5B, and FIG. 5C, the advance and retreat assist tool 100 further has the first tubular member 500 through which the treatment instrument 51 is inserted and which guides the treatment instrument 51 to the endoscope 10 via the base unit 300, and a fixing portion 600 which fixes the treatment instrument 51 to the first tubular member 500. As shown in FIG. 1A, FIG. 1B, FIG. 2A, FIG. 2B, FIG. 3A, FIG. 3B, FIG. 3C, FIG. 4A, FIG. 4B, FIG. 5A, FIG. 5B, and FIG. 5C, the advance and retreat assist tool 100 further has a rotary portion 700 provided in the first tubular member 500, and an advance and retreat mechanism 800 which advances and retreats the first tubular member 500 by a rotation force of the rotary portion 700. The advance and retreat assist tool 100 further has a regulating mechanism 900 which regulates the advance and retreat of the first tubular member 500, and a support unit 950 which supports the first tubular member 500 so that the first tubular member 500 advances and retreats by the advance and retreat mechanism 800. As shown in FIG. 1A, FIG. 1B, FIG. 1C, FIG. 5A, FIG. 5B, and FIG. 5C, the advance and retreat assist tool 100 further has a hinge mechanism 970 provided in the base unit 300 and the support unit 950.

[Base Unit 300]

Figure 2A:
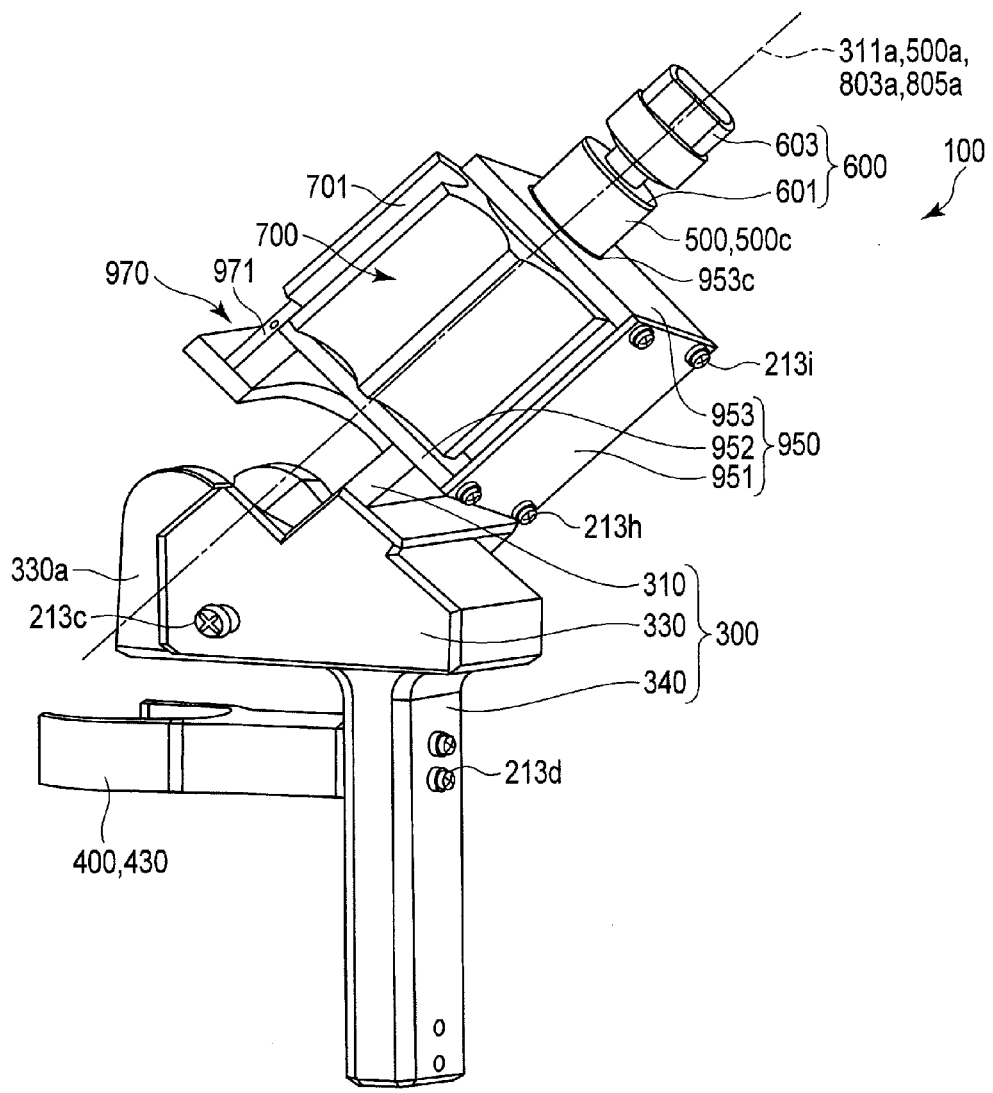
FIG. 2A is a perspective view of the advance and retreat assist tool.
Figure 2B:
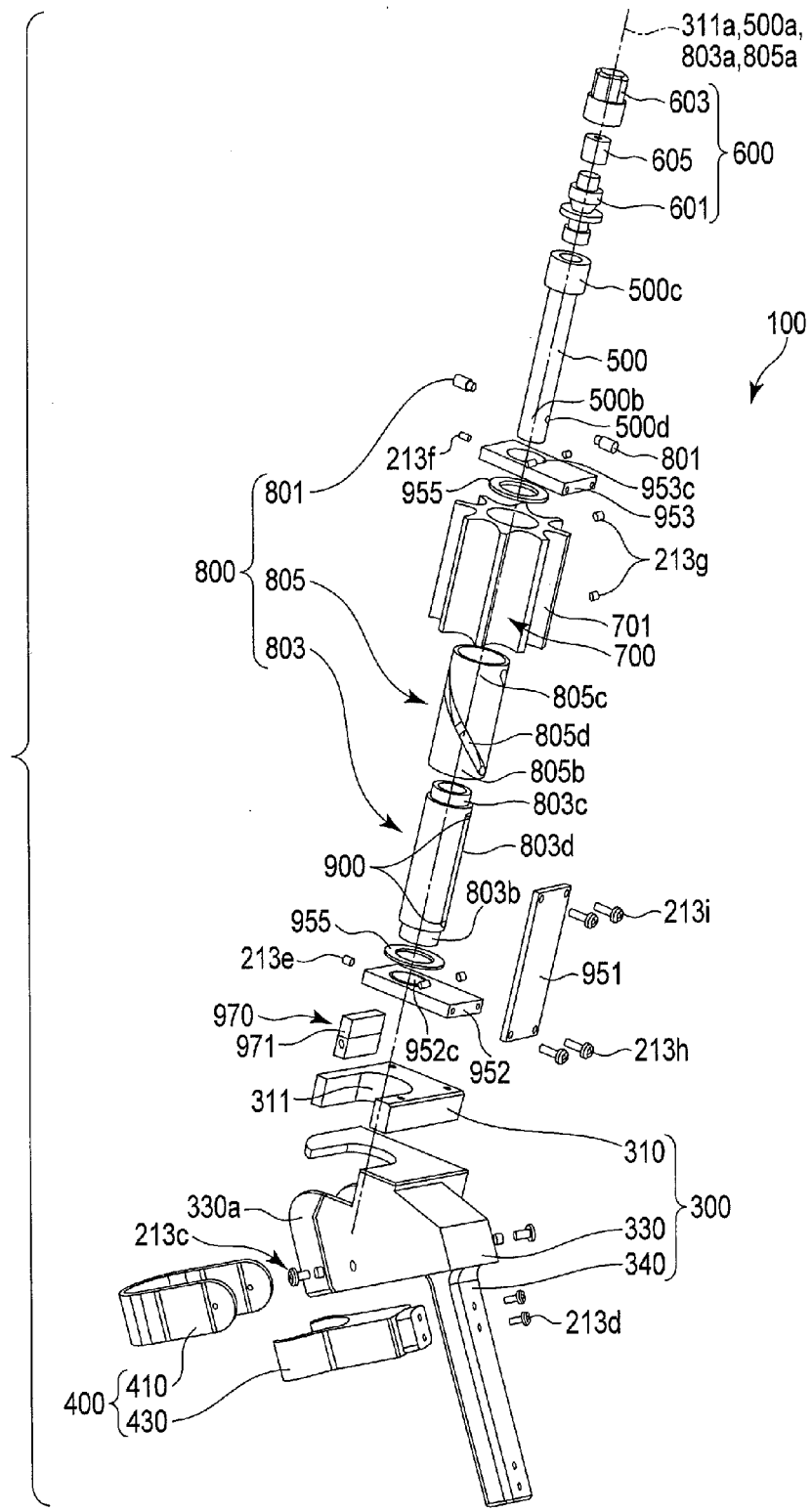
FIG. 2B is an exploded perspective view of the advance and retreat assist tool.

As shown in FIG. 1A, FIG. 1B, FIG. 2A, FIG. 2B, FIG. 3A, FIG. 3B, FIG. 4A, FIG. 4B, FIG. 5A, FIG. 5B, and FIG. 5C, the base unit 300 is removably attached to the treatment instrument insertion portion 35, the grasping portion 33, and the body portion 31 around the treatment instrument insertion hole portion 35a including the treatment instrument insertion cap 36. As shown in FIG. 2A and FIG. 2B, the base unit 300 has the U-shaped base member 310, a support member 330 which supports the base member 310, and an extension member 340 extending from the support member 330 toward the insertion portion 20 side.

As shown in FIG. 1A and FIG. 1B, the base member 310 is provided to surround the treatment instrument insertion cap 36 when the advance and retreat assist tool 100 is attached to the endoscope 10.

As shown in FIG. 1A and FIG. 1B, the support member 330 is disposed on the side of the grasping portion 33 when the advance and retreat assist tool 100 is attached to the endoscope 10.

As shown in FIG. 1A and FIG. 1B, the extension member 340 is disposed on the side of the body portion 31 when the advance and retreat assist tool 100 is attached to the endoscope 10.

[Base Member 310]

As shown in FIG. 4A and FIG. 4B, the base member 310 has the first hole portion 311 having a first central axis 311a.

Figure 1C:
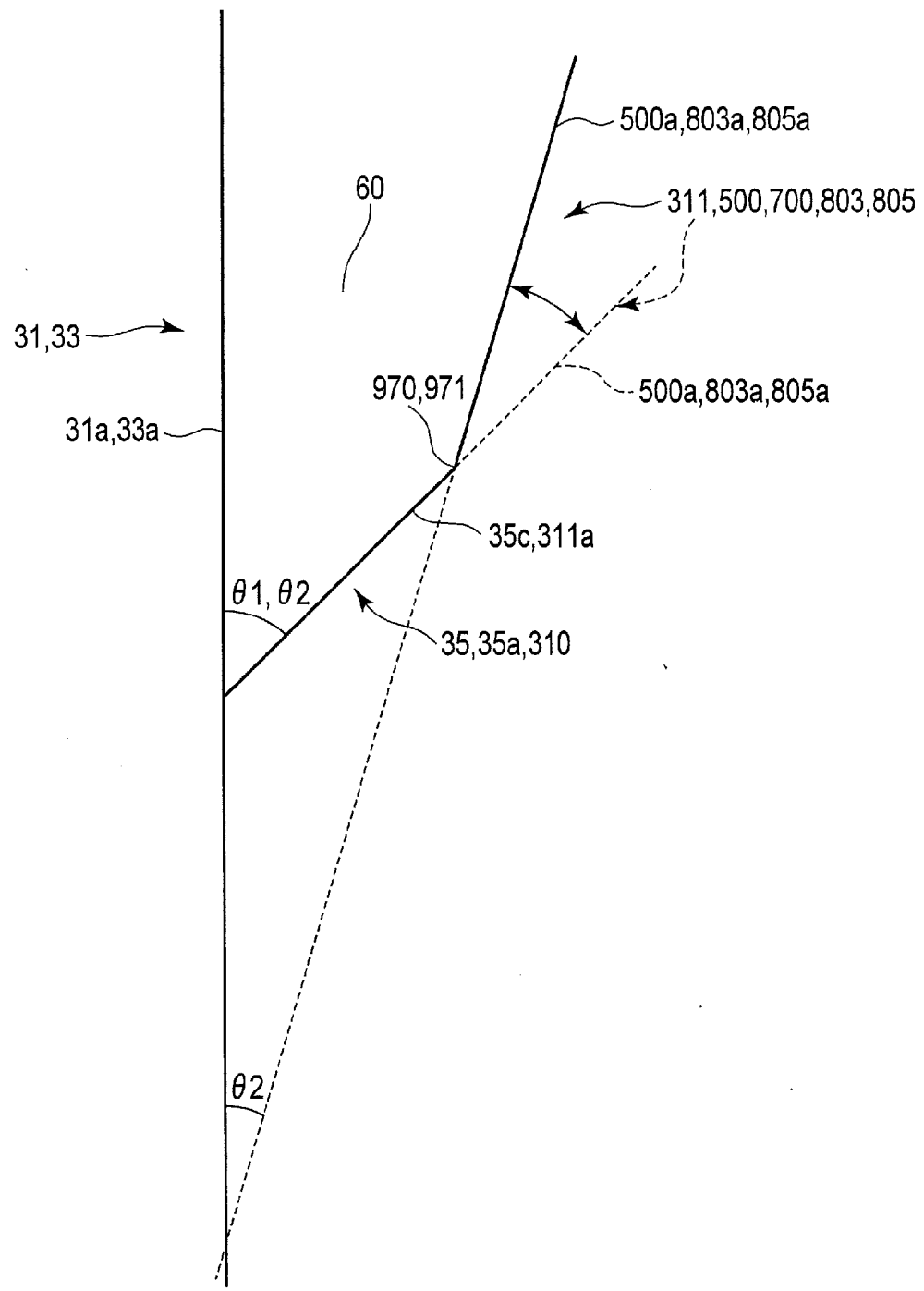
FIG. 1C is a diagram showing the relation between an angle θ1 and an angle θ2 and showing a coaxial condition and a slanted condition.

The first hole portion 311 faces the treatment instrument insertion hole portion 35a and the treatment instrument insertion channel when the advance and retreat assist tool 100 is attached to the endoscope 10. At the same time, as shown in FIG. 1A, FIG. 1B, and FIG. 1C, the first central axis 311a of the first hole portion 311 is provided coaxially with the central axis 35c of the treatment instrument insertion hole portion 35a, and is slanted relative to the central axis 33a of the grasping portion 33.

The first hole portion 311 is in communication with the outside in the direction of the first central axis 311a. The first hole portion 311 is also in communication with the outside on one side in a direction that intersects at right angles with the direction of the first central axis 311a because of the U-shaped base member 310.

In the first hole portion 311, the inner circumferential surface of the base member 310 is formed along the shape of the treatment instrument insertion cap 36, and is provided along the circumference of the central axis of the treatment instrument insertion cap 36. The inner circumferential surface is, for example, substantially U-shaped. In the base member 310 having such an inner circumferential surface, the treatment instrument insertion cap 36 is fitted into the first hole portion 311 so that the first central axis 311a is provided coaxially with the central axis of the treatment instrument insertion cap 36. The height of the base member 310 is substantially the same as the projection amount of the treatment instrument insertion cap 36 projecting from the treatment instrument insertion hole portion 35a.

As shown in FIG. 4A and FIG. 4B, the first hole portion 311 functions as a guide hole portion which guides, to the treatment instrument insertion cap 36 and the treatment instrument insertion hole portion 35a, the treatment instrument 51 which is inserted through the first tubular member 500.

As shown in FIG. 2A and FIG. 2B, the base member 310 is fixed to the support member 330 by, for example, an unshown screw portion.

[Support Member 330]

As shown in FIG. 2A and FIG. 2B, the support member 330 has a displacement prevention portion 330a which catches, for example, the treatment instrument insertion portion 35 and thereby prevents the displacement of the base unit 300 including the support member 330 when the advance and retreat assist tool 100 is attached to the endoscope 10. As shown in FIG. 1A, FIG. 1B, FIG. 2A, FIG. 2B, FIG. 4A, and FIG. 4B, the displacement prevention portion 330a prevents the displacement of the base unit 300 so that the support member 330 is provided on the side of the grasping portion 33, the extension member 340 is provided on the side of the body portion 31, the first hole portion 311 faces the treatment instrument insertion hole portion 35a, and the first central axis 311a is provided coaxially with the central axis 35c of the treatment instrument insertion hole portion 35a when the advance and retreat assist tool 100 is attached to the endoscope 10. The displacement prevention portion 330a catches the treatment instrument insertion portion 35 from the lateral side of the treatment instrument insertion portion 35. The displacement prevention portion 330a is provided on the side surface of the support member 330. The inner circumferential surface of the displacement prevention portion 330a is formed along the shape of the treatment instrument insertion portion 35, and is, for example, U-shaped, and abuts on the outer circumferential surface of the treatment instrument insertion portion 35.

[Extension Member 340]

As shown in FIG. 1A, FIG. 1B, FIG. 2A, and FIG. 2B, the extension member 340 is, for example, a bar member. The extension member 340 is integral with the support member 330. The central axis of the extension member 340 is provided parallel to a central axis 31a of the body portion 31 when the advance and retreat assist tool 100 is attached to the endoscope 10.

[Fixing Unit 400]

As shown in FIG. 1A and FIG. 1B, the fixing unit 400 fixes the base unit 300 to the endoscope 10 so that the first central axis 311a is provided coaxially with the central axis 35c of the treatment instrument insertion hole portion 35a and the first hole portion 311 faces the treatment instrument insertion hole portion 35a. The fixing unit 400 is provided in the base unit 300.

As shown in FIG. 1A, FIG. 1B, FIG. 2A, and FIG. 2B, the fixing unit 400 has a fixing portion 410 which winds around, for example, the grasping portion 33 and thereby fixes the support member 330 to the grasping portion 33 when the advance and retreat assist tool 100 is attached to the endoscope 10, and a displacement prevention portion 430 which catches, for example, the body portion 31 and thereby prevents the displacement of the base unit 300 including the extension member 340. The fixing unit 400 may include the above-mentioned base member 320.

[Fixing Portion 410]

As shown in FIG. 1A, FIG. 1B, FIG. 2A, and FIG. 2B, the fixing portion 410 winds around the grasping portion 33 after the displacement prevention portion 330a has abutted on the grasping portion 33. The fixing portion 410 is, for example, a U-shaped belt member. One end portion of the fixing portion 410 is removably fixed to one side surface of the support member 330 by, for example, a screw portion 213c. The other end portion of the fixing portion 410 is removably fixed to the other side surface of the support member 330 by, for example, the screw portion 213c.

[Displacement Prevention Portion 430]

As shown in FIG. 1A, FIG. 1B, FIG. 2A, and FIG. 2B, the displacement prevention portion 430 is fixed to the extension member 340 by, for example, a screw portion 213d to be provided along a direction that intersects at right angles with the direction of the central axis 31a of the body portion 31. The displacement prevention portion 430 is, for example, substantially Y-shaped. The inner circumferential surface of the displacement prevention portion 430 is formed along the shape of the body portion 31, and is provided along the circumference of the central axis 31a of the body portion 31. The inner circumferential surface is, for example, U-shaped, and abuts on the outer circumferential surface of the body portion 31. The displacement prevention portion 430 abuts on the body portion 31 simultaneously with the abutting of the displacement prevention portion 330a on the grasping portion 33. The displacement prevention portion 430 catches the body portion 31 from the lateral side of the body portion 31.

[First Tubular Member 500]

As shown in FIG. 4A and FIG. 4B, the first tubular member 500 has the second central axis 500a. The first tubular member 500 is provided so that the second central axis 500a can be provided along the direction of the first central axis 311a and so that the second central axis 500a can be provided coaxially with the first central axis 311a. The first tubular member 500 is formed as a cylindrical member into which the treatment instrument 51 is inserted. The treatment instrument 51 is inserted into the first tubular member 500 from a proximal end portion 500c of the first tubular member 500, and is projected from a distal end portion 500b of the first tubular member 500.

Figure 4C:
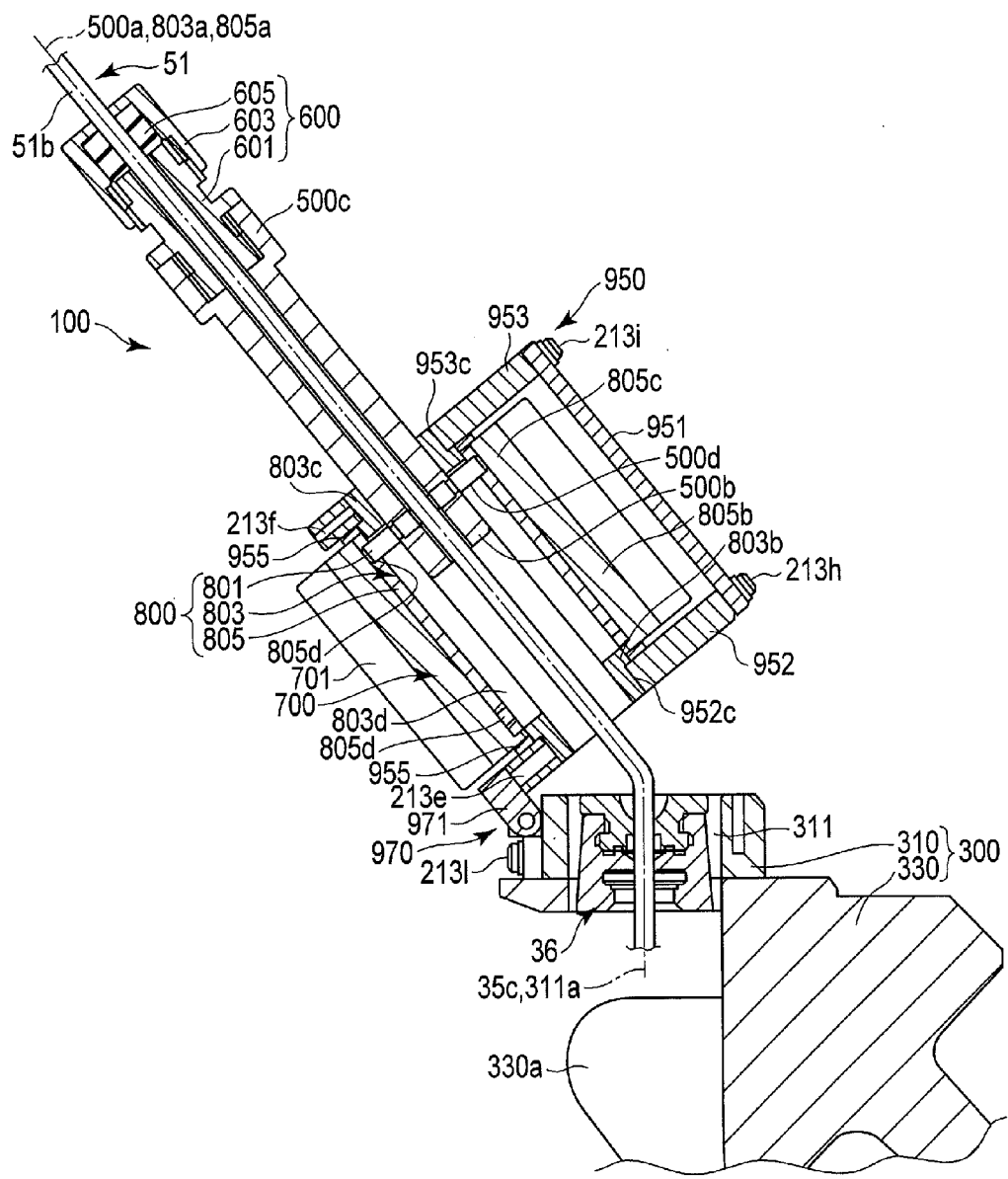
FIG. 4C is a sectional view of the advance and retreat assist tool during the retreat of the treatment instrument in the slanted condition.

As shown in FIG. 4A and FIG. 4B, the treatment instrument 51 is directly inserted into the first hole portion 311 when the first tubular member 500 advances. As shown in FIG. 4C, the treatment instrument 51 is inserted into the first hole portion 311 via a fit hole portion 952c of the support unit 950 when the first tubular member 500 retreats. That is, the first tubular member 500 functions as a guide member which guides the treatment instrument 51 to the first hole portion 311.

As shown in FIG. 2B, FIG. 4A, and FIG. 4B, the first tubular member 500 has the above-mentioned second central axis 500a, and the distal end portion 500b which is inserted into the fit hole portion 952c of the support unit 950 when the first tubular member 500 advances and which is removed from the fit hole portion 952c of the support unit 950 when the first tubular member 500 retreats. The first tubular member 500 also has the proximal end portion 500c to which a proximal end 51b of the treatment instrument 51 is fixed by the fixing portion 600. The first tubular member 500 further has an opening portion 500d which is provided in the circumferential surface of the first tubular member 500 and with which a later-described protrusion portion 801 is engaged.

As shown in FIG. 4A and FIG. 4B, the distal end portion 500b is inserted into the fit hole portion 952c of the support unit 950 so that the first tubular member 500 is in communication with the first hole portion 311 when the first tubular member 500 advances. As shown in FIG. 4C, the distal end portion 500b is removed from the fit hole portion 952c of the support unit 950 so that the first tubular member 500 faces the first hole portion 311 when the first tubular member 500 retreats.

As shown in FIG. 4A and FIG. 4B, the opening portion 500d is provided on the side of the distal end portion 500b so that the opening portion 500d is not inserted into the fit hole portion 952c of the support unit 950 when the distal end portion 500b is inserted into the fit hole portion 952c of the support unit 950. The opening portion 500d is always exposed from the fit hole portion 952c of the support unit 950. The opening portion 500d is, for example, circular. The opening portion 500d is a through-hole portion which passes through the first tubular member 500 in the thickness direction of the first tubular member 500. A pair of opening portions 500d are provided with respect to the second central axis 500a.

[Fixing Portion 600]

As shown in FIG. 2B, FIG. 3A, FIG. 3B, FIG. 4A, FIG. 4B, and FIG. 4C, the fixing portion 600 is provided at the proximal end portion 500c of the first tubular member 500. The fixing portion 600 fixes the proximal end 51b of the treatment instrument 51 to the proximal end portion 500c of the first tubular member 500. The fixing portion 600 has a cylindrical portion 601 through which the treatment instrument 51 is inserted and which is inserted into the proximal end portion 500c of the first tubular member 500, and a fixing member 605 which is mounted at the end portion of the cylindrical portion 601 and through which the treatment instrument 51 is inserted. The fixing portion 600 also has a fastening portion 603 which functions as a cap to cover the cylindrical portion 601 and the fixing member 605 and which fastens the cylindrical portion 601.

The fastening portion 603 rotates around the axis of the fastening portion 603 and thereby fastens the cylindrical portion 601, and compresses the fixing member 605 by fastening. The fixing member 605 comes into close contact with the proximal end 51b of the treatment instrument 51 by compression. As a result, the treatment instrument 51 becomes integral with the first tubular member 500 via the fixing portion 600. The fixing member 605 is formed by, for example, elastic rubber.

[Rotary Portion 700]

As shown in FIG. 1A and FIG. 1B, the rotary portion 700 rotates around the second central axis 500a. The rotary portion 700 is formed as a cylindrical member into which the first tubular member 500 is inserted. More specifically, the first tubular member 500 is inserted into the rotary portion 700 so that the central axis of the rotary portion 700 is provided coaxially with the second central axis 500a. As shown in FIG. 4A, the rotary portion 700 is rotatable around the second central axis 500a using the first tubular member 500 as a central axis while the first tubular member 500 is inserted in the rotary portion 700. As shown in FIG. 4A, the rotary portion 700 has a length such that the proximal end portion 500c of the first tubular member 500 projects outside the proximal end portion of the rotary portion 700 along the direction of the second central axis 500a when the distal end portion 500b of the first tubular member 500 is inserted in the fit hole portion 952c of the support unit 950 while the first tubular member 500 is inserted in the rotary portion 700. As shown in FIG. 1A and FIG. 1B, the rotary portion 700 is provided adjacent to the grasping portion 33 when the advance and retreat assist tool 100 is attached to the endoscope 10. Thus, the rotary portion 700 functions as an operation knob.

As shown in FIG. 1A and FIG. 1B, the rotary portion 700 has recess portions 701 provided in the outer circumferential surface of the rotary portion 700. The recess portions 701 are provided along the direction of the second central axis 500a. The recess portions 701 are adjacent to each other in a direction around the second central axis 500a. The inner circumferential surface of the recess 701 is, for example, smoothly semicircular. As shown in FIG. 5, the recess portions 701 are formed as mounting surfaces to mount the fingers of the left hand grasping the grasping portion 33.

[Configuration of Advance and Retreat Mechanism 800]

The advance and retreat mechanism 800 intervenes between the rotary portion 700 and the first tubular member 500, the advance and retreat mechanism 800 converts the rotation force of the rotary portion 700 to an advance and retreat force of the first tubular member 500, and the advance and retreat mechanism 800 transmits the advance and retreat force to the first tubular member 500 and thereby advances and retreats the first tubular member 500 along the direction of the second central axis 500a, when the rotary portion 700 rotates.

As shown in FIG. 2B, FIG. 3A, FIG. 3B, FIG. 4A, and FIG. 4B, the advance and retreat mechanism 800 has the protrusion portion 801, the second tubular member 803, and a third tubular member 805. As shown in FIG. 4A and FIG. 4B, the protrusion portion 801, the second tubular member 803, and the third tubular member 805 intervene between the first tubular member 500 and the rotary portion 700 in the diametrical direction of the first tubular member 500.

[Protrusion Portion 801]

As shown in FIG. 3A, FIG. 3B, FIG. 3C, FIG. 4A, and FIG. 4B, the protrusion portion 801 is provided straight along the diametrical direction of the first tubular member 500 so that the protrusion portion 801 passes through a later-described long opening portion 803d and is inserted into a later-described spiral opening portion 805d. The protrusion portion 801 is engaged with the opening portion 500d, and is thereby engaged with the circumferential surface of the first tubular member 500. As shown in FIG. 3C, the protrusion portion 801 has a diameter such that the protrusion portion 801 abuts on the edge portion of the long opening portion 803d and the edge portion of the spiral opening portion 805d.

[Second Tubular Member 803]

As shown in FIG. 2B, FIG. 3A, FIG. 3B, FIG. 4A, and FIG. 4B, the second tubular member 803 has a third central axis 803a, and a distal end portion 803b which is fitted into and thus fixed to the fit hole portion 952c of the support unit 950 so that the third central axis 803a can be provided along the direction of the second central axis 313a and so that the third central axis 803a can be provided coaxially with the second central axis 313a. The second tubular member 803 further has a proximal end portion 803c fitted into and thus fixed to a fit hole portion 953c of a later-described base member 953, and the long opening portion 803d provided in the circumferential surface of the second tubular member 803 along the direction of the third central axis 803a.

As shown in FIG. 4A and FIG. 4B, the distal end portion 803b is formed as a fixed end which is fixed to the base member 310 by, for example, a screw portion 213e when the distal end portion 803b is inserted in the fit hole portion 952c of the support unit 950. The screw portion 213e is inserted through the side surface of the base member 310, and abuts on the circumferential surface of the distal end portion 803b.

As shown in FIG. 4A and FIG. 4B, the proximal end portion 803c is formed as a fixed end which is fixed to the support unit 950 by, for example, a screw portion 213f when the proximal end portion 803c is inserted in the fit hole portion 953c of the support unit 950. The screw portion 213f is inserted through the side surface of the support unit 950, and abuts on the circumferential surface of the proximal end portion 803c.

As a result, the second tubular member 803 is prevented from rotating and moving, and is fixed to the base unit 300 and the support unit 950.

As shown in FIG. 2B, the long opening portion 803d is provided straight from the side of the distal end portion 803b to the side of the proximal end portion 803c. As shown in FIG. 4A and FIG. 4B, the distal end portion of the long opening portion 803d is provided on the side of the distal end portion 803b so that the distal end portion of the long opening portion 803d is not inserted into the fit hole portion 952c of the support unit 950 when the distal end portion 803b is inserted in the fit hole portion 952c of the support unit 950. As shown in FIG. 4A and FIG. 4B, the proximal end portion of the long opening portion 803d is provided on the side of the proximal end portion 803c so that the proximal end portion of the long opening portion 803d is not inserted into the fit hole portion 953c of the later-described support unit 950 when the proximal end portion 803c is inserted in the fit hole portion 953c of the support unit 950. That is, the long opening portion 803d is exposed from the fit hole portions 953c and 952c of the support unit 950.

As shown in FIG. 4A and FIG. 4B, the long opening portion 803d has a length slightly greater than the length from one edge portion of the later-described spiral opening portion 805d to the other edge portion in the direction of the third central axis 803a. One edge portion side of the long opening portion 803d faces one edge portion of the spiral opening portion 805d, and the other edge portion side of the long opening portion 803d faces the other edge portion of the spiral opening portion 805d. The long opening portion 803d is substantially equal in length to the rotary portion 700.

The length of the long opening portion 803d corresponds to the movement amount of the first tubular member 500, and corresponds to the advance and retreat amount of the treatment instrument 51. These are substantially equal in size to each other. The maximum value of the length corresponds to the maximum value of the movement amount and the maximum value of the advance and retreat amount. Each of these maximum values corresponds to the size of the part to be treated with the treatment instrument 51, and has a desired value. The maximum value is, for example, 30 mm.

The long opening portion 803d does not pass through the second tubular member 803 in the direction of the third central axis 803a. The long opening portion 803d passes through the second tubular member 803 in the thickness direction of the second tubular member 803. A pair of long opening portions 803d are provided with respect to the third central axis 803a.

Such a second tubular member 803 is formed as a cylindrical member into which the first tubular member 500 is inserted so that part of the long opening portion 803d is in communication with the opening portion 500d and the protrusion portion 801 is inserted through the long opening portion 803d. The second tubular member 803 has a length such that the proximal end portion 500c of the first tubular member 500 projects outside the proximal end portion 803c of the second tubular member 803 along the direction of the second central axis 313a when the first tubular member 500 is inserted in the second tubular member 803, the distal end portion 500b of the first tubular member 500 is inserted in the fit hole portion 952c of the support unit 950, and the distal end portion 803b of the second tubular member 803 is fitted in the fit hole portion 952c of the support unit 950.

[Third Tubular Member 805]

As shown in FIG. 2B, the third tubular member 805 has a fourth central axis 805a provided coaxially with the second central axis 500a, and a distal end portion 805b. The third tubular member 805 also has a proximal end portion 805c, and the spiral opening portion 805d provided in the circumferential surface of the third tubular member 805 to wind around the fourth central axis 805a.

As shown in FIG. 4A and FIG. 4B, the third tubular member 805 is provided so that the distal end portion 805b is not inserted into the fit hole portion 952c of the support unit 950 and the proximal end portion 805c is not inserted into the fit hole portion 953c of the support unit 950.

As shown in FIG. 4A and FIG. 4B, the third tubular member 805 is inserted into the rotary portion 700 so that the third tubular member 805 rotates relative to the second tubular member 803 around the fourth central axis 805*a* together with the rotary portion 700. The third tubular member 805 is fixed to the rotary portion 700 by a screw portion 213*g* shown in FIG. 2B so that the third tubular member 805 rotates together with the rotary portion 700. Thus, the third tubular member 805 rotates in the same direction as the rotary portion 700. As shown in FIG. 3C, FIG. 4A, and FIG. 4B, the third tubular member 805 functions as a cylindrical member into which the second tubular member 803 is inserted so that part of the spiral opening portion 805*d* is in communication with part of the long opening portion 803*d* and so that the protrusion portion 801 inserted through the long opening portion 803*d* is inserted into the spiral opening portion 805*d*. Such a third tubular member 805 functions as a cam ring. The third tubular member 805 is substantially equal in length to the long opening portion 803*d* and the rotary portion 700.

As shown in FIG. 2B, the spiral opening portion 805*d* is provided from the distal end portion 805*b* to the proximal end portion 805*c* in the direction of the fourth central axis 805*a*. The spiral opening portion 805*d* does not pass through the third tubular member 805 in the direction of the fourth central axis 805*a*. The spiral opening portion 805*d* passes through the third tubular member 805 in the thickness direction of the third tubular member 805. A pair of spiral opening portions 805*d* are provided with respect to the second central axis 500*a*.

[Operation of Advance and Retreat Mechanism 800]

As shown in FIG. 1A, FIG. 1B, FIG. 3A, FIG. 3B, FIG. 3C, FIG. 4A, and FIG. 4B, if the rotary portion 700 rotates around the second central axis 500*a*, the third tubular member 805 also rotates simultaneously with the rotary portion 700. As a result, the spiral opening portion 805*d* provided in the third tubular member 805 also rotates.

As shown in FIG. 3A and FIG. 3B, the protrusion portion 801 is in abutment with the edge portion of the spiral opening portion 805*d*. Thus, in response to the rotation of the spiral opening portion 805*d*, the protrusion portion 801 is pressed to rotate by the spiral opening portion 805*d*. As shown in FIG. 3A and FIG. 3B, the protrusion portion 801 is inserted through the long opening portion 803*d*, and is also in abutment with the edge portion of the long opening portion 803*d*. Thus, the protrusion portion 801 is pressed to rotate by the spiral opening portion 805*d*, so that the protrusion portion 801 moves in the long opening portion 803*d* along the direction of the second central axis 500*a*.

Thus, the third tubular member 805 rotates together with the rotation of the rotary portion 700, so that the spiral opening portion 805*d* rotates. As a result of the rotation of the spiral opening portion 805*d*, the protrusion portion 801 moves in the long opening portion 803*d* along the direction of the second central axis 500*a* by the spiral opening portion 805*d*.

The protrusion portion 801 abuts on the edge portion of the long opening portion 803*d*, so that the first tubular member 500 having the distal end portion 500*b* with which the protrusion portion 801 is engaged is prevented from rotating around the second central axis 500*a*.

The spiral opening portion 805*d* rotates, and the protrusion portion 801 moves in the long opening portion 803*d* along the direction of the second central axis 500*a*, so that the first tubular member 500 having the distal end portion 500*b* with which the protrusion portion 801 is engaged advances and retreats along the direction of the second central axis 500*a* while the rotation of the first tubular member 500 around the second central axis 500*a* is prevented. As a result, the treatment instrument 51 fixed to the first tubular member 500 advances and retreats.

The distal end portion 803*b* of the second tubular member 803 is fitted into and thus fixed to the fit hole portion 952*c* of the support unit 950, and the proximal end portion 803*c* of the second tubular member 803 is fitted into and thus fixed to the fit hole portion 953*c* of the support unit 950. Therefore, the second tubular member 803 remains fixed. This prevents the long opening portion 803*d* from rotating in the same manner as the spiral opening portion 805*d*.

The protrusion portion 801 only moves in the long opening portion 803*d* along the direction of the second central axis 500*a*. Therefore, the first tubular member 500 only advances and retreats along the direction of the second central axis 500*a*, and the rotation of the first tubular member 500 around the second central axis 500*a* is prevented. Similarly, the treatment instrument 51 only advances and retreats, and the rotation of the treatment instrument 51 around the second central axis 500*a* is prevented.

Thus, the advance and retreat mechanism 800 advances and retreats the treatment instrument 51 while the treatment instrument 51 is prevented from rotating around the second central axis 500*a* in response to the rotation of the rotary portion 700 around the second central axis 500*a* when the rotary portion 700 rotates around the second central axis 500*a*.

[Regulating Mechanism 900]

The regulating mechanism 900 regulates the advance and retreat of the first tubular member 500 when the first tubular member 500 advances and retreats along the direction of the second central axis 500*a* so that the distal end portion 500*b* of the first tubular member 500 moves along the direction of the second central axis 500*a* between a part where the first hole portion 311 provided on the distal end portion side of the rotary portion 700 is in communication with the fit hole portion 952*c* of the support unit 950 and a position on the side where the first tubular member 500 provided on the proximal end portion side of the rotary portion 700 comes off the rotary portion 700.

The regulating mechanism 900 is formed by the protrusion portion 801 and by the edge portion of the spiral opening portion 805*d*.

[Support Unit 950]

As shown in FIG. 1A, FIG. 1B, FIG. 2A, FIG. 2B, FIG. 3A, FIG. 3B, FIG. 4A, and FIG. 4B, the support unit 950 supports the first tubular member 500 via the protrusion portion 801, the second tubular member 803, and the third tubular member 805 so that the second central axis 500*a* is able to be provided coaxially with the second central axis 313*a*, the first tubular member 500 advances and retreats along the direction of the second central axis 500*a*, and thus the first tubular member 500 is prevented from moving in a direction that intersects at right angles with the direction of the second central axis 500*a*.

The support unit 950 has a base member 951 which is provided along the direction of the second central axis 500*a* and which is provided on the side of the rotary portion 700, and a base member 952 which is provided along the direction that intersects at right angles with the direction of the second central axis 500*a* and which is provided under the rotary portion 700. The support unit 950 further has the base member 953 which is provided along the direction that intersects at right angles with the direction of the second central axis 500*a* and which is provided above the rotary portion 700.

The base member 951 has one end portion fixed to the base member 952 by, for example, a screw portion 213*h*, and the other end portion fixed to the base member 953 by, for example, a screw portion 213*i*.

The base member 952 has the fit hole portion 952*c* into which the distal end portion 803*b* of the second tubular member 803 is fitted. The base member 952 is fixed by, for example, a screw portion 213*j* to the distal end portion 803*b* of the second tubular member 803 which is fitted into the fit hole portion 952*c*.

The base member 952 is mountable on the base member 310 so that the fit hole portion 952*c* is in communication with the first hole portion 311 and the treatment instrument insertion cap 36 and so that the central axis of the fit hole portion 952*c* can be provided coaxially with the first central axis 311*a*.

The base member 952 functions as a support base member having the fit hole portion 952*c* that is an insertion/removal hole portion which the first tubular member 500 is inserted into and removed from when the first tubular member 500 advances and retreats.

The base member 953 has the fit hole portion 953*c* into which the proximal end portion 803*c* of the second tubular member 803 is fitted. The base member 953 is fixed by, for example, a screw portion 213*f* to the proximal end portion 803*c* of the second tubular member 803 which is fitted into the fit hole portion 953*c*.

The support unit 950 supports the first tubular member 500 via the second tubular member 803. The support unit 950 supports the third tubular member 805 via the second tubular member 803 and a washer 955.

[Hinge Mechanism 970]

Figure 5C:
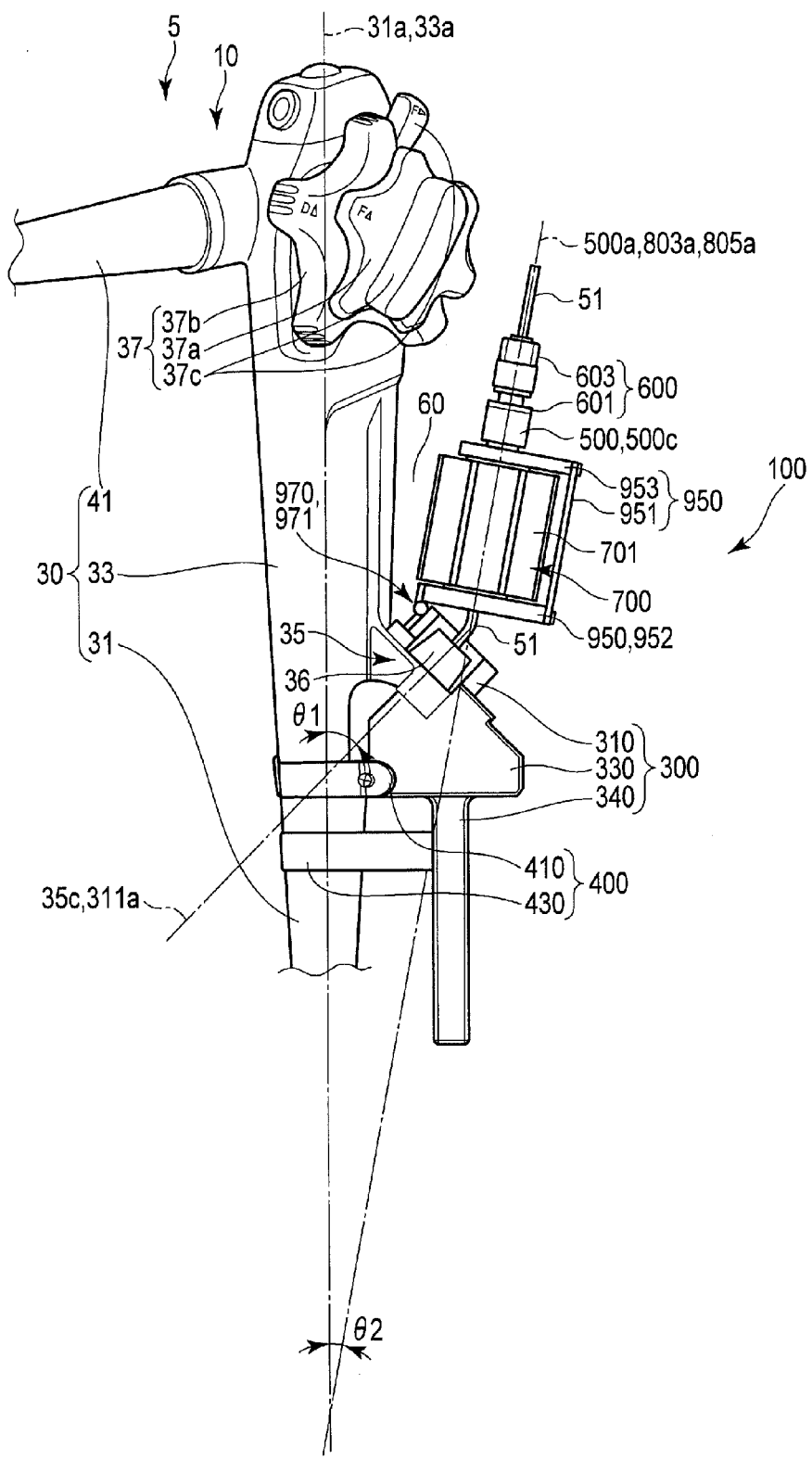
FIG. 5C is a schematic diagram in which the angle θ1>the angle θ2, the condition is the slanted condition, the clearance between the grasping portion and the rotation portion is smallest, and the endoscope is grasped and the treatment instrument is advanced and retreated with one hand at the same time.

The hinge mechanism 970 switches to either a coaxial condition shown in FIG. 4A and FIG. 5B or a slanted condition shown in FIG. 1A, FIG. 1B, FIG. 4B, FIG. 4C, FIG. 5A, and FIG. 5C, and fixes the slanted condition when the hinge mechanism 970 has switched to the slanted condition.

As shown in FIG. 4A and FIG. 5B, the coaxial condition shows a condition where the treatment instrument 51 is inserted into or removed from the endoscope 10 and where the central axis of the fixing portion 600, the third central axis 803*a*, the fourth central axis 805*a*, the central axis of the rotary portion 700, and the second central axis 500*a* is provided coaxially with the first central axis 311*a*.

As shown in FIG. 1A, FIG. 1B, FIG. 4B, FIG. 4C, FIG. 5A, and FIG. 5C, the slanted condition shows a condition where the treatment instrument 51 advances and retreats in response to the operation of the rotary portion 700 and where the central axis of the fixing portion 600, the third central axis 803*a*, the fourth central axis 805*a*, the central axis of the rotary portion 700, and the second central axis 500*a* is slanted relative to the first central axis 311*a*.

As described above and as shown in FIG. 1C, the first central axis 311*a* of the first hole portion 311 is provided coaxially with the central axis 35*c* of the treatment instrument insertion hole portion 35*a*, and is slanted relative to the central axis 33*a* of the grasping portion 33.

As shown in FIG. 1C, an angle formed between the direction of the central axis 35*c* of the treatment instrument insertion hole portion 35*a* (the direction of the first central axis 311*a* of the first hole portion 311) and the direction of the central axis 33*a* of the grasping portion 33 is an angle $\theta 1$.

As shown in FIG. 1C, an angle formed between the central axis of the fixing portion 600, the third central axis 803*a*, the fourth central axis 805*a*, the central axis of the rotary portion 700, and the second central axis 500*a*, and the direction of the central axis 33*a* of the grasping portion 33 is an angle $\theta 2$.

As shown in FIG. 5B, the hinge mechanism 970 rotates the support unit 950 relative to the base unit 300 in the coaxial condition so that the angle $\theta 1$=the angle $\theta 2$.

This condition shows a condition where the support unit 950 including the first tubular member 500, the fixing portion 600, the rotary portion 700, and the advance and retreat mechanism 800 is provided coaxially with the base member 310 apart from the grasping portion 33 and where a clearance 60 between the grasping portion 33 and the rotary portion 700 is widest and where the distance between the grasping portion 33 and the rotary portion 700 is longest. Thus, the angle $\theta 1=\theta 2$ is formed when the treatment instrument 51 does not need to be advanced and retreated and when the rotary portion 700 is not operated, and shows an angle at which the interruption of grasping by the advance and retreat assist tool 100 is eliminated.

As shown in FIG. 5C, the hinge mechanism 970 rotates the support unit 950 relative to the base unit 300 in the slanted condition so that the rotary portion 700 is adjacent to the grasping portion 33, so that the central axis of the fixing portion 600, the third central axis 803*a*, the fourth central axis 805*a*, the central axis of the rotary portion 700, and the second central axis 500*a* is provided substantially parallel to the central axis of the grasping portion 33, and so that the angle $\theta 1$>the angle $\theta 2$.

This condition is a condition where the support unit 950 including the first tubular member 500, the fixing portion 600, the rotary portion 700, and the advance and retreat mechanism 800 is slanted relative to the base member 310 closer to the grasping portion 33 and where the clearance 60 between the grasping portion 33 and the rotary portion 700 is widest and where the distance between the grasping portion 33 and the rotary portion 700 is shortest and where the rotary portion 700 is adjacent to the grasping portion 33. Thus, the angle $\theta 1$>the angle $\theta 2$ is an angle which is formed when the rotary portion 700 is operated to advance and retreat the treatment instrument 51 and which allows one hand to grasp the endoscope 10 and advance and retreat the treatment instrument 51 at the same time.

As shown in FIG. 5B, the hinge mechanism 970 rotates the support unit 950 relative to the base unit 300 in the coaxial condition so that the first hole portion 311 faces the first tubular member 500, and so that the support unit 950 including the first tubular member 500, the fixing portion 600, the rotary portion 700, and the advance and retreat mechanism 800 faces the base unit 300. In this case, in the direction of the central axis 35*c* of the treatment instrument insertion hole portion 35*a*, the base member 952 is mounted on the base member 310 and provided above the treatment instrument insertion cap 36 so that the fit hole portion 952*c* is in communication with the first hole portion 311 and the treatment instrument insertion cap 36.

As shown in FIG. 5C, the hinge mechanism 970 rotates the support unit 950 relative to the base unit 300 in the slanted condition so that the support unit 950 including the first tubular member 500, the fixing portion 600, the rotary portion 700, and the advance and retreat mechanism 800 is slanted toward the grasping portion 33 relative to the base unit 300. In this case, the base member 952 rotates toward the grasping portion 33 relative to the base unit 310, and is then provided aslant relative to the treatment instrument insertion cap 36.

The hinge mechanism 970 also rotates the support unit 950 relative to the base unit 300 so that the fit hole portion 952*c* which is the insertion/removal hole portion is in communication with the first hole portion 311 and the treatment instrument insertion cap 36 in the coaxial condition and so that the fit hole portion 952c is slanted relative to the first hole portion 311 in the slanted condition.

[Hinge Member 971]

As shown in FIG. 4A, FIG. 4B, and FIG. 4C, the hinge mechanism 970 has a free-stop-type hinge member 971 which is fixed to the side surface of the base member 310 and the side surface of the base member 952 by, for example, a screw portion 213l. The hinge member 971 rotates the base member 952 relative to the base member 310 in the case of an external force equal to or more than a desired value, and fixes the slanted condition in the case of an external force equal to or less than the desired value in the slanted condition.

The side surface of the base member 310 and the side surface of the base member 952 are provided flush together. These side surfaces function as the center of rotation together, and the hinge member 971 functions as a rotation central axis. The side surfaces are provided along the direction of the first central axis 311a. It is preferable that the distance between the side surface of the base member 310 and the first hole portion 311 is short in a direction that intersects at right angles with the first central axis 311a. It is also preferable that the distance between the side surface of the base member 952 and the fit hole portion 952c is short in a direction that intersects at right angles with the second central axis 500a.

[Functions]

[Attachment of Advance and Retreat Assist Tool 100 to Endoscope 10]

As shown in FIG. 1A, FIG. 1B, FIG. 4A, and FIG. 4B, the fixing unit 400 fixes the base unit 300 to the endoscope 10 so that the first hole portion 311 faces the treatment instrument insertion hole portion 35a.

At the same time, the displacement prevention portion 330a catches the treatment instrument insertion portion 35 and thereby prevents the displacement of the base unit 300 including the support member 330. The displacement prevention portion 330a also prevents the displacement of the base unit 300 so that the base member 310 surrounds the treatment instrument insertion cap 36 in the first hole portion 311, the first hole portion 311 faces the treatment instrument insertion hole portion 35a, and the first central axis 311a of the first hole portion 311 is provided coaxially with the central axis 35c of the treatment instrument insertion hole portion 35a. The fixing portion 410 winds around the grasping portion 33, and fixes the support member 330 to the grasping portion 33. The displacement prevention portion 430 catches the body portion 31 and thereby prevents the displacement of the base unit 300 including the extension member 340.

As shown in FIG. 4A and FIG. 5B, the hinge mechanism 970 including the hinge member 971 rotates the support unit 950 including the first tubular member 500, the fixing portion 600, the rotary portion 700, and the advance and retreat mechanism 800 toward the base member 310 to reach the coaxial condition, that is, to reach the angle θ1=the angle θ2. As a result, the support unit 950 including the first tubular member 500, the fixing portion 600, the rotary portion 700, and the advance and retreat mechanism 800 is mounted on the base member 310 and provided above the treatment instrument insertion cap 36, and the first tubular member 500 is brought into communication with the treatment instrument insertion cap 36.

[Provision of Treatment Instrument 51]

In the coaxial condition, after the insertion portion 20 of the endoscope 10 is inserted into the body cavity, the treatment instrument 51 is inserted from the fixing portion 600, and inserted through the first tubular member 500. The treatment instrument 51 is further inserted into the endoscope 10 from the treatment instrument insertion portion 35. The distal end portion 51a of the treatment instrument 51 then projects from the distal opening portion 35b. The length of the projecting distal end portion 51a of the treatment instrument 51 is a desired length.

The fastening portion 603 rotates around the axis of the fastening portion 603 and thereby fastens the cylindrical portion 601, and compresses the fixing member 605 by fastening. The fixing member 605 comes into close contact with the proximal end 51b of the treatment instrument 51 by compression. As a result, the treatment instrument 51 is fixed to the advance and retreat assist tool 100 via the fixing portion 600 and the first tubular member 500.

When the treatment instrument 51 is removed from the endoscope 10, this operation is performed in the procedure reverse to the above procedure in the coaxial condition.

In the case described above, the base member 952 is not slanted relative to the base member 310, the second central axis 500a is provided coaxially with the central axis of the treatment instrument insertion cap 36, and the first tubular member 500 is brought into communication with the treatment instrument insertion cap 36. Thus, the treatment instrument 51 is inserted into or removed from the endoscope 10 without resistance in the base members 310 and 952.

[Grasping of Endoscope 10 and Treatment Instrument 51]

The grasping portion 33 is grasped by the left hand of the surgeon.

[When Advance and Retreat Operations of Treatment Instrument 51 are not Needed]

As shown in FIG. 5B, in the coaxial condition, the support unit 950 including the first tubular member 500, the fixing portion 600, the rotary portion 700, and the advance and retreat mechanism 800 is provided coaxially with the base member 310 apart from the grasping portion 33, the clearance 60 between the grasping portion 33 and the rotary portion 700 is widest, and the distance between the grasping portion 33 and the rotary portion 700 is longest. Thus, the interruption of grasping by the advance and retreat assist tool 100 is eliminated. In this respect, the interruption of insertion and removal by the advance and retreat assist tool 100 is also eliminated when the above-mentioned treatment instrument 51 is inserted into or removed from the endoscope 10.

[When Treatment Instrument 51 is Operated to Advance and Retreat]

As shown in FIG. 1A FIG. 1B, FIG. 5A, and FIG. 5C, the hinge mechanism 970 including the hinge member 971 rotates the support unit 950 including the first tubular member 500, the fixing portion 600, the rotary portion 700, and the advance and retreat mechanism 800 toward the grasping portion 33 relative to the base member 310 to reach the slanted condition, that is, to reach the angle θ1>the angle θ2 while the treatment instrument 51 is inserted in the endoscope 10. As a result, the support unit 950 including the first tubular member 500, the fixing portion 600, the rotary portion 700, and the advance and retreat mechanism 800 is adjacent to the grasping portion 33. At the same time, the hinge member 971 fixes the slanted condition in the case of an external force equal to or less than the desired value.

As shown in FIG. 5A, the rotary portion 700 is adjacent to the grasping portion 33 is operated by, for example, the little finger or third finger of the left hand grasping the grasping portion 33, and the bending operation portion is operated by the thumb of the left hand. In this instance, as shown in FIG. 5C, the angle θ1>the angle θ2, so that the clearance 60 between the grasping portion 33 and the rotary portion 700 is smallest, the distance between the grasping portion 33 and the rotary portion 700 is shortest, and the rotary portion 700 is provided adjacent to the grasping portion 33. The endoscope 10 is grasped and the treatment instrument 51 is advanced and retreated with one hand at the same time.

[Advance Operation of Treatment Instrument 51]

When the rotary portion 700 is operated by, for example, the little finger or third finger of the left hand, the rotary portion 700 rotates in one direction around the second central axis 500a. At the same time, the third tubular member 805 also rotates in the same manner as the rotary portion 700. As a result, the spiral opening portion 805d provided in the third tubular member 805 also rotates.

As a result of the rotation of the spiral opening portion 805d, the protrusion portion 801 moves in the long opening portion 803d along the direction of the second central axis 500a by the spiral opening portion 805d.

The first tubular member 500 having the distal end portion 500b with which the protrusion portion 801 is engaged advances along the direction of the second central axis 500a. As a result, the treatment instrument 51 fixed to the first tubular member 500 advances.

Since the second tubular member 803 is fixed, the long opening portion 803d is fixed, so that the long opening portion 803d is prevented from rotating in the same manner as the spiral opening portion 805d. Therefore, the protrusion portion 801 only moves in the long opening portion 803d along the direction of the second central axis 500a. Therefore, the first tubular member 500 only advances along the direction of the second central axis 500a, and the rotation of the first tubular member 500 around the second central axis 500a is prevented. Similarly, the treatment instrument 51 only advances, and the rotation of the treatment instrument 51 around the second central axis 500a is prevented.

The protrusion portion 801 abuts on one edge portion of the spiral opening portion 805d, so that the advance of the first tubular member 500 is stopped, and the advance of the treatment instrument 51 is stopped.

[Retreat Operation of Treatment Instrument 51]

When the rotary portion 700 is operated by, for example, the little finger or third finger of the left hand, the rotary portion 700 rotates in the other direction around the second central axis 500a. At the same time, the third tubular member 805 also rotates in the same manner as the rotary portion 700. As a result, the spiral opening portion 805d provided in the third tubular member 805 also rotates.

As a result of the rotation of the spiral opening portion 805d, the protrusion portion 801 moves in the long opening portion 803d along the direction of the second central axis 500a by the spiral opening portion 805d.

The first tubular member 500 having the distal end portion 500b with which the protrusion portion 801 is engaged retreats along the direction of the second central axis 500a. As a result, the treatment instrument 51 fixed to the first tubular member 500 retreats.

Since the second tubular member 803 is fixed, the long opening portion 803d is fixed, so that the long opening portion 803d is prevented from rotating in the same manner as the spiral opening portion 805d. Therefore, the protrusion portion 801 only moves in the long opening portion 803d along the direction of the second central axis 500a. Therefore, the first tubular member 500 only retreats along the direction of the second central axis 500a, and the rotation of the first tubular member 500 around the second central axis 500a is prevented. Similarly, the treatment instrument 51 only retreats, and the rotation of the treatment instrument 51 around the second central axis 500a is prevented.

The protrusion portion 801 abuts on the other edge portion of the spiral opening portion 805d, so that the retreat of the first tubular member 500 is stopped, and the retreat of the treatment instrument 51 is stopped. This also prevents the first tubular member 500 from coming off the rotary portion 700.

[Advantageous Effects]

Thus, according to the present embodiment, the condition is switched to either the coaxial condition or the slanted condition by the hinge mechanism 970, and the slanted condition is fixed when the condition is switched to the slanted condition.

In the slanted condition where the angle $\theta 1$>the angle $\theta 2$, the support unit 950 including the first tubular member 500, the fixing portion 600, the rotary portion 700, and the advance and retreat mechanism 800 is slanted relative to the base member 310 closer to the grasping portion 33, the rotary portion 700 is provided substantially parallel to the grasping portion 33, the rotary portion 700 is adjacent to the grasping portion 33, and where the clearance 60 between the grasping portion 33 and the rotary portion 700 can be widest. Thus, according to the present embodiment, when the treatment instrument 51 is operated to advance and retreat, the fingers of the hand grasping the grasping portion 33 reach the rotary portion 700 without fail, the surgeon is not burdened, the operation is easier, and the endoscope 10 can be grasped and the treatment instrument 51 can be operated to advance and retreat with one hand at the same time. Moreover, according to the present embodiment, it is possible to prevent the whole endoscope 10 from increasing in size without causing problems to the smooth one-handed advance and retreat operations.

As described above, the slanted condition is fixed. Thus, according to the present embodiment, the operation of fixing the slant is eliminated, and the surgeon can concentrate on the grasping operation of the grasping portion and the advance and retreat operations of the treatment instrument.

In the coaxial condition, the base member 952 is not slanted relative to the base member 310, the second central axis 500a is provided coaxially with the central axis of the treatment instrument insertion cap 36, and the first tubular member 500 is brought into communication with the treatment instrument insertion cap 36. Thus, according to the present embodiment, the treatment instrument 51 can be inserted into or removed from the endoscope 10 without resistance in the base members 310 and 952.

In the coaxial condition, the support unit 950 including the first tubular member 500, the fixing portion 600, the rotary portion 700, and the advance and retreat mechanism 800 is provided coaxially with the base member 310 apart from the grasping portion 33, and the clearance 60 between the grasping portion 33 and the rotary portion 700 can be widest. Thus, according to the present embodiment, when the treatment instrument 51 is not advanced and retreated, the interruption of grasping by the advance and retreat assist tool 100 is eliminated.

As described above, the present embodiment enables simple one-handed operations, smooth one-handed advance and retreat operations, fixing of the slant, and reduction of resistance during the advance and retreat of the treatment instrument.

According to the present embodiment, the bending operation portion 37 and the switch portion 39 are provided in the grasping portion 33. Thus, according to the present embodiment, the surgeon can operate the bending operation portion 37 and the switch portion 39 while grasping the endoscope 10 and advancing and retreating the treatment instrument 51 with one hand at the same time.

According to the present embodiment, the hinge member 971 enables the above to be achieved at low cost with a simple configuration. Moreover, according to the present embodiment, the hinge member 971 can quickly and stably switch between the coaxial condition and the slanted condition.

According to the present embodiment, the second central axis 500a is slanted relative to the first central axis 311a in the slanted condition, and the rotary portion 700 rotates around the second central axis 500a. The advance and retreat mechanism 800 converts the rotation force of the rotary portion 700 to an advance and retreat force, and advances and retreats the first tubular member 500 by the advance and retreat force. Thus, according to the present embodiment, it is possible to prevent the size increase of the endoscope 10, ensure that the treatment instrument 51 is finely advanced and retreated by one hand grasping the grasping portion 33, and prevent a burden on the surgeon.

More specifically, according to the present embodiment, in the advance and retreat mechanism 800, the rotation force of the rotary portion 700 is not transmitted directly to the first tubular member 500, converted to an advance and retreat force by the second tubular member 803 and the third tubular member 805, and transmitted indirectly to the first tubular member 500. Thus, according to the present embodiment, it is possible to prevent the treatment instrument 51 from rapidly advancing and retreating, and finely advance and retreat the treatment instrument 51.

According to the present embodiment, the treatment instrument 51 can be advanced and retreated by the advance and retreat mechanism 800 without rotating together with the rotary portion 700.

According to the present embodiment, the protrusion portion 801 abuts on the edge portion of the spiral opening portion 805d, so that the advance and retreat of the first tubular member 500 can be regulated, and the advance and retreat of the treatment instrument 51 can be regulated.

The long opening portion 803d may have a length slightly smaller than the length from one edge portion of the spiral opening portion 805d to the other edge portion in the direction of the third central axis 803a. In this case, the protrusion portion 801 abuts on the edge portion of the long opening portion 803d, so that the advance and retreat of the first tubular member 500 can be regulated, and the advance and retreat of the treatment instrument 51 can be regulated. The regulating mechanism 900 is then formed by the protrusion portion 801 and by the edge portion of the long opening portion 803d.

The long opening portion 803d may have a length substantially equal to the length from one edge portion of the spiral opening portion 805d to the other edge portion in the direction of the third central axis 803a. In this case, one edge portion of the long opening portion 803d faces one edge portion of the spiral opening portion 805d, and the other edge portion of the long opening portion 803d faces the other edge portion of the spiral opening portion 805d. In this case, the protrusion portion 801 abuts on the edge portion of the long opening portion 803d and the edge portion of the spiral opening portion 805d, so that the advance and retreat of the first tubular member 500 can be regulated, and the advance and retreat of the treatment instrument 51 can be regulated. The regulating mechanism 900 is then formed by the protrusion portion 801, the edge portion of the long opening portion 803d, and the end portion of the spiral opening portion 805d.

Thus, the regulating mechanism 900 has only to be formed by at least one of the protrusion portion 801, the end portion of the spiral opening portion 805d, and the edge portion of the long opening portion 803d.

According to the present embodiment, the support unit 950 can prevent the first tubular member 500 from moving in a direction that intersects at right angles with the direction of the second central axis 500a. Thus, according to the present embodiment, the first tubular member 500 and the treatment instrument 51 can be advanced and retreated.

According to the present embodiment, it is possible to freely adjust the advance and retreat amount of the treatment instrument 51 by setting the length of the long opening portion 803d and the length of the spiral opening portion 805d to desired lengths.

According to the present embodiment, for example, the first tubular member 500 may have an unshown index which is provided on the outer circumferential surface of the first tubular member 500 and which indicates the advance and retreat position of the treatment instrument 51. When the first tubular member 500 is exposed from the rotary portion 700 in accordance with the advance and retreat, the index portion is exposed from the rotary portion 700. Thus, the surgeon can recognize the advance and retreat position of the treatment instrument 51 by checking the index portion.

[First Modification]

A first modification of the first embodiment is now described with reference to FIG. 6. In the present modification, components different from the above components alone are described below.

[Configuration]

In the present modification, the hinge mechanism 970 has a hinge member 973 which is fixed to the side surface of the base member 310 and the side surface of the base member 952 by, for example, an unshown screw portion and which rotates the base member 952 relative to the base member 310, and a screw member 975 which is fastened into the hinge member 973 and thereby fixes the slanted condition.

[Advantageous Effects]

According to the present modification, it is possible to further ensure that the slanted condition is fixed by the hinge member 973 and the screw member 975.

[Second Modification]

A second modification of the first embodiment is now described with reference to FIG. 7A and FIG. 7B. In the present modification, components different from the above components alone are described below.

[Configuration]

In the present modification, as shown in FIG. 7A and FIG. 7B, the hinge mechanism 970 has the above-mentioned hinge member 973, and a guide groove portion 977 provided in one of the base member 310 and the base member 952. The hinge mechanism 970 further has a protrusion portion 979 which is provided in the other of the base member 310 and the base member 952 and which slides on the guide groove portion 977 in response to the rotation of the base member 952 relative to the base member 310, and a lock portion 981 which is provided in the guide groove portion 977 and which locks the protrusion portion 979 and thereby fixes the slanted condition.

In the present modification, the base member 310 has a depressed section, and the flat base member 952 is fitted in the base member 310.

The guide groove portion 977 and the protrusion portion 979 are provided in the side surface different from the side surface to which the hinge member 973 is attached. For example, the guide groove portion 977 is provided in the inner circumferential surface of the base member 310, and the protrusion portion 979 is provided on the side surface of the base member 952 facing the above inner circumferential surface. The guide groove portion 977 has, for example, a quarter-circular-arc shape.

Although one hinge mechanism 970 is shown for clarity of illustration in FIG. 7A, another hinge mechanism 970 may be provided on the opposite side.

The lock portion 981 is a protrusion portion provided at one end portion of the guide groove portion 977. As indicated by a broken line in FIG. 7B, the protrusion portion 979 climbs over the lock portion 981 which is the protrusion portion, and is then held between the edge portion at one end portion of the guide groove portion 977 and the lock portion 981, so that the lock portion 981 locks the protrusion portion 979.

[Advantageous Effects]

According to the present modification, the protrusion portion 979 slides on the guide groove portion 977, so that the base member 952 can smoothly rotate relative to the base member 310 without shaking. Moreover, according to the present modification, the lock portion 981 locks the protrusion portion 979, which further ensures that the slanted condition is fixed.

The lock portion 981 may be provided at the other end portion of the guide groove portion 977, and so as to fix the slanted condition.

[Third Modification]

A third modification of the first embodiment is now described with reference to FIG. 8A and FIG. 8B. In the present modification, components different from the above components alone are described below.

[Configuration]

In the present modification, the hinge mechanism 970 has a rotation central axis member 983 which is held to the base member 310 through the base member 952 and which functions as a rotation center for the base member 952 to rotate relative to the base member 310, the above-mentioned guide groove portion 977, the above-mentioned protrusion portion 979, and the above-mentioned lock portion 981.

The rotation central axis member 983 is, for example, a cylindrical rod member.

In the present modification, the base member 310 has a depressed section, and the base member 952 is T-shaped and is mounted on the base member 310.

[Advantageous Effects]

According to the present modification, the hinge member 973 can be omitted, which simplifies the configuration.

[Fourth Modification]

Figure 9A:
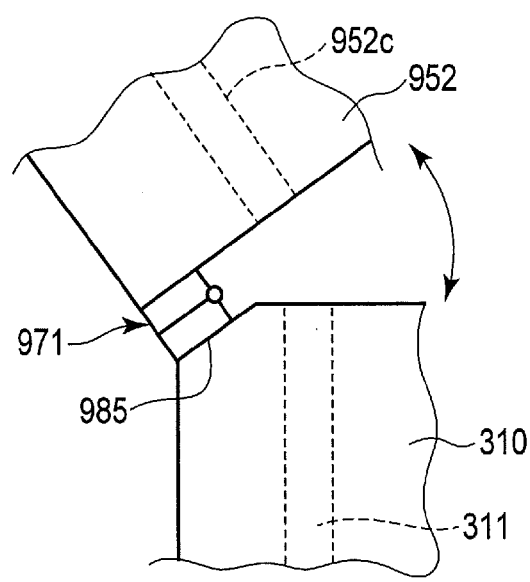
FIG. 9A is a diagram showing the hinge mechanism according to a fourth modification of the first embodiment and is a diagram showing the slanted condition.
Figure 9B:
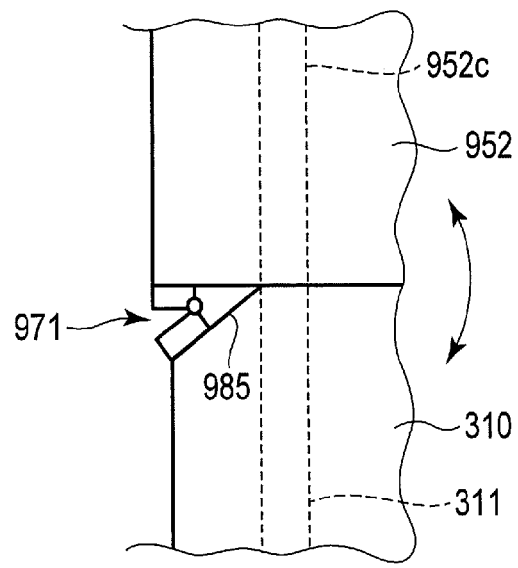
FIG. 9B is a diagram showing the hinge mechanism according to the fourth modification of the first embodiment and is a diagram showing the coaxial condition.

A fourth modification of the first embodiment is now described with reference to FIG. 9A and FIG. 9B. In the present modification, only components that differ from the above components are described below.

[Configuration]

For example, in the base member 310, a slanted surface 985 is formed. The end portion of the slanted surface 985 functions as the center of rotation, and is located in the vicinity of the first hole portion 311 and the fit hole portion 952c. The hinge member 971 is attached to the slanted surface 985.

[Advantageous Effects]

According to the present modification, the center portion of rotation is located in the vicinity of the first hole portion 311 and the fit hole portion 952c, so that the advance and retreat assist tool 100 can be compact in the slanted condition.

[Fifth Modification]

A fifth modification of the first embodiment is now described with reference to FIG. 10. In the present modification, components different from the above components alone are described below.

[Configuration]

The hinge mechanism 970 further has a corrugated protective member 987 which expands in the slanted condition and contracts in the coaxial condition and which protects part of the treatment instrument 51. Such part of the treatment instrument 51 refers to a part which is provided between the base member 310 and the base member 952 and which is exposed from the first tubular member 500 and the treatment instrument insertion cap 36.

The protective member 987 prevents, for example, dust in the atmosphere from entering the first hole portion 311, the treatment instrument insertion cap 36, the first tubular member 500, and the fit hole portion 952c. The protective member 987 has one end portion attached to the base member 310, and the other end portion attached to the base member 952. The protective member 987 surrounds a space provided between the base member 310 and the base member 952 in the slanted condition, and tightly encloses the space.

[Advantageous Effects]

According to the present modification, the protective member 987 can protect part of the treatment instrument 51, and prevent, for example, dust in the atmosphere from entering the first hole portion 311, the treatment instrument insertion cap 36, the first tubular member 500, and the fit hole portion 952c.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An advance and retreat assist tool for an endoscopic treatment instrument, the advance and retreat assist tool comprising:
    a base unit including a part where the endoscopic treatment instrument to be inserted into an endoscope passes, the base unit being fixed to the endoscope to face a treatment instrument insertion hole portion of the endoscope;
    a first tubular member provided coaxially with a central axis of the treatment instrument insertion hole portion, the endoscopic treatment instrument being inserted into and fixed to the first tubular member;
    a rotary portion into which the first tubular member is inserted, the rotary portion rotates around an axis of the first tubular member;
    an advance and retreat mechanism configured to convert a rotation force during the rotation of the rotary portion to an advance and retreat force along an axial direction of the first tubular member to advance and retreat the first tubular member;
    a support unit which supports the first tubular member so that the first tubular member is advanced and retreated by the advance and retreat mechanism; and a hinge mechanism pivotally connecting the base unit and the support unit, the hinge mechanism pivots the support unit between a first position and a second position, wherein:
in the first position, an axis of the rotary portion is provided coaxially with the central axis of the treatment instrument insertion hole portion;
in the second position, the axis of the rotary portion is slanted relative to the central axis of the treatment instrument insertion hole portion; and
the endoscopic treatment instrument is inserted into or removed from the endoscope in the first position, and the rotary portion is operated to advance and retreat the endoscopic treatment instrument in the second position.

2. The advance and retreat assist tool for the endoscopic treatment instrument according to claim 1, wherein the hinge mechanism is fixed in the second position so as to be slanted when the hinge mechanism switches to the second position.

3. The advance and retreat assist tool for the endoscopic treatment instrument according to claim 2, wherein the hinge mechanism includes a member that rotates the support unit relative to the base unit by an external force that is applied equal to or greater than a desired value, the member fixes the hinge mechanism in to be slanted by an external force equal to or less than the desired value.

4. The advance and retreat assist tool for the endoscopic treatment instrument according to claim 2, wherein the hinge mechanism includes:
a guide groove portion provided in the base unit, and a protrusion portion that slides on the guide groove portion; and
a lock portion provided in the guide groove portion, the lock portion locks the protrusion portion and fixes the support unit in the second position.

5. The advance and retreat assist tool for the endoscopic treatment instrument according to claim 1, wherein
the central axis of the treatment instrument insertion hole portion is slanted at an angle $\theta 1$ relative to a central axis of a grasping portion of the endoscope in which the treatment instrument insertion hole portion is provided;
an angle formed between the axis of the first tubular member and the central axis of the grasping portion is an angle $\theta 2$; and
the angle $\theta 1$>the angle $\theta 2$ so that the rotary portion is adjacent to the grasping portion in the second position.

6. The advance and retreat assist tool for the endoscopic treatment instrument according to claim 1, wherein the hinge mechanism rotates the support unit relative to the base unit so that:
the support unit including the first tubular member, the rotary portion, and the advance and retreat mechanism faces the base unit in the coaxial condition, and
the support unit including the first tubular member, the rotary portion, and the advance and retreat mechanism is slanted relative to the base unit toward a grasping portion of the endoscope in which the treatment instrument insertion hole portion is provided in the second position.

7. The advance and retreat assist tool for the endoscopic treatment instrument according to claim 1, wherein
the base unit further comprises a first hole portion through which the endoscopic treatment instrument passes, the first hole portion having a first central axis; and
the advance and retreat assist tool for the endoscopic treatment instrument further comprising a fixing unit which fixes the base unit to the endoscope so that the first central axis of the first hole portion is provided coaxially with the central axis of the treatment instrument insertion hole portion, and the first hole portion faces the treatment instrument insertion hole portion.

8. The advance and retreat assist tool for the endoscopic treatment instrument according to claim 1, wherein the advance and retreat mechanism intervenes between the rotary portion and the first tubular member.

9. The advance and retreat assist tool for the endoscopic treatment instrument according to claim 8, wherein the advance and retreat mechanism includes:
a protrusion portion which is provided straight along a diametrical direction of the first tubular member, the protrusion portion is engaged with the circumferential surface of the first tubular member;
a second tubular member having a long opening portion through which the protrusion portion is inserted, the second tubular member being fixed to the support unit, the first tubular member being inserted into the second tubular member; and
a third tubular member having a spiral opening portion provided in the circumferential surface, the second tubular member being inserted into the third tubular member so that part of the spiral opening portion is in communication with part of the long opening portion and so that the protrusion portion, which is inserted through the long opening portion, is inserted into the spiral opening portion, the third tubular member being coaxial with the rotary portion, and the third tubular member rotating together with the rotary portion.

10. The advance and retreat assist tool for the endoscopic treatment instrument according to claim 9, wherein
the third tubular member rotates in response to the rotation of the rotary portion causing the spiral opening portion to rotate;
the protrusion portion moves in the long opening portion along the axial direction of the first tubular member as a result of the rotation of the spiral opening portion;
the protrusion portion abuts on an edge portion of the long opening portion so that the first tubular member, with which the protrusion portion is engaged, is prevented from rotating around the axis of the rotary portion; and
the spiral opening portion rotates, and the protrusion portion moves in the long opening portion, so that the first tubular member advances and retreats in the axial direction of the rotary portion while the rotation of the first tubular member around the axis of the rotary portion is prevented.

11. The advance and retreat assist tool for the endoscopic treatment instrument according to claim 1, further comprising a regulating mechanism which regulates the advance and retreat of the first tubular member to prevent the first tubular member from losing contact with the rotary portion when the first tubular member advances and retreats along the axial direction of the rotary portion.

12. The advance and retreat assist tool for the endoscopic treatment instrument according to claim 1, wherein a proximal end portion of the first tubular member projects outside a proximal end portion of the rotary portion along the axial direction of the rotary portion.

13. The advance and retreat assist tool for the endoscopic treatment instrument according to claim 1, wherein the support unit supports the first tubular member such that the axis of the rotary portion is provided coaxially with the axis of the first tubular member and such that the first tubular member advances and retreats along a direction of the axis of the rotary portion, and the first tubular member is prevented from moving in a direction that intersects perpendicular to the axis of the rotary portion.

* * * * *